United States Patent
Sinclair et al.

(10) Patent No.: US 11,278,726 B2
(45) Date of Patent: *Mar. 22, 2022

(54) SYSTEMS AND METHODS FOR MONITORING NEURAL ACTIVITY

(71) Applicant: DEEP BRAIN STIMULATION TECHNOLOGIES PTY, LTD., East Melbourne (AU)

(72) Inventors: Nicholas Sinclair, East Melbourne (AU); Hugh McDermott, East Melbourne (AU); James Fallon, East Melbourne (AU); Thushara Perera, East Melbourne (AU); Arthur Wesley Thevathasan, East Melbourne (AU); Kristian Bulluss, East Melbourne (AU)

(73) Assignee: DEEP BRAIN STIMULATION TECHNOLOGIES PTY LTD, East Melbourne (AU)

( * ) Notice: Subject to any disclaimer, the term of this patent is extended or adjusted under 35 U.S.C. 154(b) by 147 days.

This patent is subject to a terminal disclaimer.

(21) Appl. No.: 16/555,376

(22) Filed: Aug. 29, 2019

(65) Prior Publication Data

US 2019/0381317 A1    Dec. 19, 2019

Related U.S. Application Data

(63) Continuation of application No. 16/195,294, filed on Nov. 19, 2018, now Pat. No. 10,463,860, which is a
(Continued)

(30) Foreign Application Priority Data

Aug. 8, 2016   (AU) .................. 2016903116

(51) Int. Cl.
*A61N 1/05*   (2006.01)
*A61N 1/36*   (2006.01)
(Continued)

(52) U.S. Cl.
CPC ............ *A61N 1/36139* (2013.01); *A61B 5/24* (2021.01); *A61B 5/377* (2021.01); *A61B 5/4842* (2013.01);
(Continued)

(58) Field of Classification Search
CPC ......... A61B 5/24; A61B 5/377; A61B 5/4842; A61B 5/6868; A61N 1/0534; A61N 1/36;
(Continued)

(56) References Cited

U.S. PATENT DOCUMENTS 5,561,526 A   10/1996   Huber et al.
5,966,473 A   10/1999   Takahashi et al.
(Continued)

FOREIGN PATENT DOCUMENTS

AU   2007281311 A1   2/2008
AU   2002340189 B2   8/2008
(Continued)

OTHER PUBLICATIONS

Al-Ani et al., Automatic removal of high-amplitude stimulus artefact from neuronal signal recorded in the subthalamic nucleus, J. Neuroscience Methods, 198:135-46 (2011).
(Continued)

*Primary Examiner* — George Manuel

(57) ABSTRACT

A method of monitoring neural activity responsive to a stimulus in a brain, the method comprising: applying the stimulus to one or more of at least one electrode implanted in a target neural structure of the brain; detecting a resonant response from the target neural structure evoked by the stimulus at one or more of the at least one electrode in or near the target neural structure of the brain; and determining one or more waveform characteristics of the detected resonant response.

28 Claims, 23 Drawing Sheets

Related U.S. Application Data continuation of application No. PCT/AU2017/050809, filed on Aug. 2, 2017.

(51) Int. Cl.
| | |
|---|---|
| *A61N 1/375* | (2006.01) |
| *A61B 5/00* | (2006.01) |
| *A61B 5/24* | (2021.01) |
| *A61B 5/377* | (2021.01) |

(52) U.S. Cl.
CPC .......... *A61B 5/6868* (2013.01); *A61N 1/0534* (2013.01); *A61N 1/36* (2013.01); *A61N 1/36067* (2013.01); *A61N 1/36167* (2013.01); *A61N 1/36178* (2013.01); *A61N 1/37514* (2017.08); *A61N 1/36064* (2013.01); *A61N 1/36185* (2013.01)

(58) Field of Classification Search
CPC ............ A61N 1/36064; A61N 1/36067; A61N 1/36139; A61N 1/36167; A61N 1/36178; A61N 1/36185; A61N 1/37514
See application file for complete search history.

(56) References Cited

U.S. PATENT DOCUMENTS

| | | | |
|---|---|---|---|
| 6,066,163 | A | 5/2000 | John |
| 6,137,491 | A | 10/2000 | Szeliski |
| 6,463,328 | B1 | 10/2002 | John |
| 6,480,743 | B1 | 11/2002 | Kirkpatrick et al. |
| 6,922,632 | B2 | 7/2005 | Foxlin |
| 6,985,238 | B2 | 1/2006 | Isaacs et al. |
| 7,639,741 | B1 | 12/2009 | Holt et al. |
| 7,768,656 | B2 | 8/2010 | Lapa et al. |
| 7,912,673 | B2 | 3/2011 | Hebert et al. |
| 7,983,757 | B2 | 7/2011 | Miyazawa et al. |
| 8,032,327 | B2 | 10/2011 | Hebert et al. |
| 8,082,120 | B2 | 12/2011 | St-Pierre et al. |
| 8,121,399 | B2 | 2/2012 | Hayashi et al. |
| 8,190,251 | B2 | 5/2012 | Molnar et al. |
| 8,662,676 | B1 | 3/2014 | Chang et al. |
| 8,791,997 | B2 | 7/2014 | Munkelt et al. |
| 8,798,764 | B2 | 8/2014 | Molnar et al. |
| 8,892,208 | B2 | 11/2014 | Flynn et al. |
| 8,914,119 | B2 | 12/2014 | Wu et al. |
| 9,325,973 | B1 | 4/2016 | Hazeghi et al. |
| 9,338,447 | B1 | 5/2016 | Crump et al. |
| 10,463,860 | B2 | 11/2019 | Sinclair et al. |
| 10,463,862 | B2 | 11/2019 | LeBaron et al. |
| 2002/0097906 | A1 | 7/2002 | Ishiyama |
| 2002/0135165 | A1 | 9/2002 | Zayan et al. |
| 2003/0097159 | A1 | 5/2003 | Schiff et al. |
| 2003/0234941 | A1 | 12/2003 | Mundy et al. |
| 2004/0057057 | A1 | 3/2004 | Isaacs et al. |
| 2004/0153129 | A1 | 8/2004 | Pless et al. |
| 2004/0252230 | A1 | 12/2004 | Winder |
| 2005/0021104 | A1 | 1/2005 | DiLorenzo |
| 2006/0062449 | A1 | 3/2006 | Pratt |
| 2006/0104495 | A1 | 5/2006 | Cathier et al. |
| 2006/0276722 | A1 | 12/2006 | Litvak et al. |
| 2007/0103646 | A1 | 5/2007 | Young |
| 2007/0142874 | A1 | 6/2007 | John |
| 2007/0183666 | A1 | 8/2007 | Ding |
| 2008/0004537 | A1 | 1/2008 | Uutela |
| 2008/0075324 | A1 | 3/2008 | Sato et al. |
| 2008/0097658 | A1 | 4/2008 | Shue et al. |
| 2008/0201101 | A1 | 8/2008 | Hebert et al. |
| 2008/0234783 | A1* | 9/2008 | van den Honert .......... A61N 1/36038 607/57 |
| 2008/0285843 | A1 | 11/2008 | Lim |
| 2009/0097039 | A1 | 4/2009 | Kawasaki et al. |
| 2009/0205088 | A1 | 8/2009 | Crampton et al. |
| 2009/0238449 | A1 | 9/2009 | Zhang et al. |
| 2010/0125315 | A1 | 5/2010 | Parramon et al. |
| 2010/0142805 | A1 | 6/2010 | Maxwell et al. |
| 2010/0142818 | A1 | 6/2010 | Stein et al. |
| 2010/0142825 | A1 | 6/2010 | Maxwell et al. |
| 2010/0142846 | A1 | 6/2010 | Tolliver et al. |
| 2010/0204748 | A1 | 8/2010 | Lozano et al. |
| 2011/0028859 | A1 | 2/2011 | Chian |
| 2011/0134225 | A1 | 6/2011 | Saint-Pierre et al. |
| 2011/0137371 | A1 | 6/2011 | Giftakis et al. |
| 2012/0016435 | A1 | 1/2012 | Rom |
| 2012/0065699 | A1 | 3/2012 | Bedenbaugh |
| 2012/0099798 | A1 | 4/2012 | Saruta et al. |
| 2012/0150257 | A1 | 6/2012 | Aur et al. |
| 2012/0271375 | A1 | 10/2012 | Wu et al. |
| 2013/0053722 | A1 | 2/2013 | Carlson et al. |
| 2013/0150918 | A1 | 6/2013 | Peterson et al. |
| 2014/0163627 | A1 | 6/2014 | Starr et al. |
| 2014/0236257 | A1 | 8/2014 | Parker et al. |
| 2014/0243926 | A1 | 8/2014 | Carcieri |
| 2014/0276195 | A1 | 9/2014 | Papay et al. |
| 2015/0238765 | A1 | 8/2015 | Zhu |
| 2016/0074663 | A1 | 3/2016 | De Ridder |

FOREIGN PATENT DOCUMENTS

| | | |
|---|---|---|
| AU | 2014351064 B2 | 7/2019 |
| CA | 2656163 C | 7/2011 |
| CN | 101026776 A | 8/2007 |
| CN | 101292131 B | 7/2011 |
| CN | 102338616 A | 2/2012 |
| CN | 101611291 B | 4/2012 |
| CN | 101620676 B | 5/2012 |
| CN | 102263920 B | 5/2014 |
| EP | 1385426 B1 | 6/2005 |
| EP | 1335668 B1 | 7/2006 |
| EP | 1575664 B1 | 2/2010 |
| JP | H08136220 A | 5/1996 |
| JP | H1021401 A | 1/1998 |
| JP | 2000175176 A | 6/2000 |
| JP | 2002521683 A | 7/2002 |
| JP | 2009283917 A | 12/2009 |
| JP | 2012026974 A | 2/2012 |
| JP | 2016-77520 A | 5/2016 |
| WO | WO-99/60525 A1 | 11/1999 |
| WO | WO-02/30510 A1 | 4/2002 |
| WO | WO-2004/043536 A1 | 5/2004 |
| WO | WO-2009/009724 A1 | 1/2009 |
| WO | WO-2011/119251 A2 | 9/2011 |
| WO | WO-2012168904 A3 | 2/2013 |
| WO | WO-2013/123112 A1 | 8/2013 |
| WO | WO-2015/069632 A1 | 5/2015 |
| WO | WO-2015/070281 A1 | 5/2015 |
| WO | WO-2015/079324 A2 | 6/2015 |
| WO | WO-2016/205231 A1 | 12/2016 |
| WO | WO-2018/005981 A1 | 1/2018 |
| WO | WO-2018/027259 A1 | 2/2018 |

OTHER PUBLICATIONS

Eusebio et al., Resonance in subthalamo-cortical circuits in Parkinson's disease, Brain, 132(Pt.8):2139-50 (Aug. 2009).

International Application No. PCT/AU2017/050809, International Search Report and Written Opinion, dated Nov. 29, 2017.

International Application No. PCT/AU2017/050809, Third Party Observation, submitted Dec. 6, 2018.

Kent et al., Recording evoked potentials during deep brain stimulation: development and validation of instrumentation to suppress the stimulus artefact, J. Neural Eng., 9(3):036004 (Jun. 2012).

Westlye et al., Increased hippocampal default mode synchronization during rest in middle-aged and elderly APOE e4 carriers: relationships with memory performance, J. Neurosci., 31(21):7775-83 (May 2011).

International Search Report issued in PCT Patent Application No. PCT/AU2019/050407 dated Jul. 11, 2019.

Written Opinion issued in PCT Patent Application No. PCT/AU2018/050486 dated Sep. 18, 2018.

(56) References Cited

OTHER PUBLICATIONS

International Search Report issued in PCT Patent Application No. PCT/AU2018/050486 dated Sep. 18, 2018.
Zaehle et al., "Resonance phenomena in the human auditory cortex: individual resonance frequencies of the cerebral cortex determining electrophysiological responses," *Experimental Brain Research*, vol. 203, No. 3 (May 7, 2010).
Blais, F., "Review of 20 years of range sensor development," *Journal of Electronic Imaging*, vol. 13(1) (Jan. 2004).
Zhang, L. et al., "Rapid Shape Acquisition Using Color Structured Light and Multi-Pass Dynamic Programming," https://grail.cs.washington.edu/projects/moscan/paper.pdf.
Vuylsteke, P. et al., "Range Image Acquisition with a Single Binary-Encoded Light Pattern," *IEEE Transaction on Pattern Analysis and Machine Intelligence*, vol. 12, No. 2 (Feb. 1990).
Heikkila, J., "Geometric Camera Calibration Using Circular Control Points," *IEEE Transactions on Pattern Analysis and Machine Intelligence*, vol. 22, No. 10 (Oct. 2000).
Ouellet, J. et al., "Geometric Calibration of a Structured Light System Using Circular Control Points" *Proceedings of the Fourth 3D Data Processing Visualization and Transmission*, pp. 1-8 (Jun. 2008).
Salvi, J. et al., "Pattern Codification Strategies in Structured Light Systems," *Pattern Recognition*, vol. 37, pp. 827-849, (2004).
Trucco, E. et al., "Introductory Techniques for 3-D Computer Vision," pp. 292-293, (1998).
Gelfand, N. et al., "Geometrically Stable Sampling for the ICP Algorithm," Fourth International Conference on 3D Digital Imaging and Modeling, 9 pages (Oct. 2003).
Gelfand, N. et al., "Shape Segmentation Using Local Slippage Analysis," *Eurographics Symposium on Geometry Processing* (2004).
Herbert, P., "A Self-Referenced Hand-Held Range Sensor," *IEEE, Third International Conference on 3 D Digital Imaging and Modeling*, pp. 5-12 (2001).
Guehring, J. "Reliable 3D Surface Acquisition, Registration and Validation Using Statistical Error Models," *IEEE, Third International Conference on 3 D Digital Imaging and Modeling*, pp. 224-231 (2001).
Newcombe, R. et al., "KinectFusion: Real-Time Dense Surface Mapping and Tracking," *IEEE International Symposium on Mixed and Augmented Reality* (*ISMAR*), pp. 127-136 (2011).
Choi, C. et al., "Voting-based Pose Estimation for Robotic Assembly Using a 3D Sensor," *IEEE International Conference on Robotics and Automation* (*ICRA*), pp. 1824-1831 (2012).
Notice of Reasons for Rejection issued in Japanese Patent Application No. 2019-529299 dated Jun. 21, 2021.

\* cited by examiner

SYSTEMS AND METHODS FOR MONITORING NEURAL ACTIVITY

TECHNICAL FIELD

The present disclosure relates to deep brain stimulation (DBS) and, in particular, methods and systems of monitoring neural activity responsive to DBS.

BACKGROUND

Deep brain stimulation (DBS) is an established therapy for movement disorders as well as other neurological disorders, including epilepsy, obsessive compulsive disorder, and depression. DBS is typically administered to patients whose symptoms cannot be adequately controlled by medication alone. DBS involves surgically implanting electrodes in or near to specific neural structures of the brain, typically in the subthalamic nucleus (STN), the globus pallidus interna (GPi), and/or the thalamus. Electrodes are connected to a neurostimulator usually implanted within the body and configured to deliver electrical pulses into target areas. It is believed that this electrical stimulation disrupts abnormal brain activity causally linked to a patient's symptoms. Stimulation parameters can be adjusted using a controller external to the body, remotely connected to the neurostimulator.

Whilst established DBS technology has proven to be effective in alleviating movement disorder symptoms, there are several limitations to state of the art devices. In particular, established techniques for intraoperative testing of DBS electrodes to ensure correct positioning in the brain, such as x-ray imaging, microelectrode recordings, and clinical assessment can be inaccurate. Consequently, electrodes are often implanted in suboptimal locations, resulting in diminished therapeutic outcomes and unwanted side-effects. After implantation, DBS devices require manual adjustment by a clinician. This typically involves the clinician adjusting parameters of the stimulus based on a largely subjective assessment of immediate or short-term improvement of the patient's symptoms. Since therapeutic effects can be slow to emerge and because the DBS parameter space is large, the task of finding a preferred set of parameters is time- and cost-inefficient, and can lead to suboptimal therapeutic outcomes. In addition, the constant, non-varying application of electrical stimulation using conventional DBS can also lead to suboptimal therapeutic outcomes, including unwanted side effects, as well as reduced battery life of DBS stimulators.

SUMMARY

According to a first aspect of the disclosure, there is provided a method of monitoring neural activity responsive to a stimulus in a brain, the method comprising: applying the stimulus to one or more of at least one electrode implanted in the brain; detecting a resonant response from the target neural structure evoked by the stimulus at one or more of the at least one electrode in or near a target neural structure of the brain; and determining one or more waveform characteristics of the detected resonant response.

The one or more waveform characteristics may be determined based on at least part of a second or subsequent cycle in the detected resonant response.

The one or more waveform characteristics may comprise one or more of the following: a) a frequency of the resonant response; b) a temporal envelope of the resonant response; c) an amplitude of the resonant response; d) a fine structure of the resonant response; e) a rate of decay of the resonant response; f) a delay between the onset of the stimulus and the onset of a temporal feature of the resonant response.

The stimulus may comprise a plurality of pulses.

The step of determining the one or more waveform characteristics may comprise comparing a first characteristic over two or more cycles of the detected resonant response. The step of determining the one or more waveform characteristics may comprise determining a change of the first characteristic over the two or more cycles. The step of determining the one or more waveform characteristics may comprise determining a rate of change of the first characteristic over the two or more cycles.

The resonant response may comprise a plurality of resonant components. One or more of the plurality of resonant components from a neural structure different from the target neural structure.

The method may further comprise adjusting the location of one or more of the at least one electrodes based on the one or more determined waveform characteristics.

The method may further comprise adapting the stimulus based on the one or more determined waveform characteristics of the resonant response. The adapting may comprise adjusting one or more of the frequency, amplitude, pulse-width, electrode configuration, or morphology of the stimulus.

The method may further comprise correlating the detected resonant response with a template resonant response; and adapting the stimulus based on the correlation. The method may further comprise correlating the one or more determined waveform characteristics with one or more predetermined threshold values; and adapting the stimulus based on the correlation.

The stimulus may be non-therapeutic or therapeutic.

The stimulus may comprise a patterned signal comprising a plurality of bursts separated by a first time period, each burst comprising a plurality of pulses separated by a second time period, wherein the first time period is greater than the second time period and wherein the detecting is performed during one or more of the first time periods. The first time period may be greater than or equal to the second time period. The plurality of pulses within at least one of the bursts may have different amplitudes. The different amplitudes may be selected to produce a ramp in amplitude of sequential pulses in the at least one of the bursts. The final pulse in each of the plurality of bursts may be substantially identical.

The method may further comprise: estimating a patient state of a patient based on the determined one or more waveform characteristics. In which case, the method may further comprise diagnosing the patient based on the estimate of the patient's state and/or generating one or more alerts associated with the estimated patient state; and outputting the one or more alerts.

The method may further comprise applying a second stimulus to a target neural structure in the brain; detecting a second resonant response from the target neural structure evoked by the second stimulus at one or more of the at least one electrode implanted in or near the target neural structure; determining one or more second waveform characteristics of the detected second resonant response.

The method may further comprise: estimating a degree of progression of a disease associated with the patient based on the one or more first waveform characteristics and the one or more second waveform characteristics.

The method may further comprise: determining the effect of a therapy provided to the patient based on the one or more first waveform characteristics and the one or more second waveform characteristics. The therapy may be medication or deep brain stimulation.

The at least one electrode may comprise two or more electrodes located within different neural structures in the brain. The at least one electrode may comprise two or more electrodes located within different hemispheres of the brain.

The method may further comprising: determining whether one or more of the at least one electrode is positioned in the target neural network based on the detected resonant response. The method may further comprise moving one or more of the first electrode and the second electrode based on the detected resonant response.

The steps of applying the stimulus, detecting a resonant response and determining one or more waveform characteristics of the detected resonant response, may be repeated one or more times so that a series of resonant responses are detected, each in response to application of a separate signal. These steps may be repeated until it is determined that one or more of the at least one electrode is positioned in the target neural structure.

The method may further comprise comparing a common waveform characteristic between two or more detected resonant responses.

The method may further comprise comparing a degree of change of a common characteristic between two or more detected resonant responses.

The method may further comprise determining a rate of change of a common characteristic between two or more detected resonant responses.

The method may further comprise selecting one or more of the at least one electrode to use for therapeutic stimulation of the target neural structure based on the one or more waveform characteristics; and applying a therapeutic stimulus to the target neural structure via the selected one or more of the at least one electrode.

The method may further comprise: inserting the at least one electrode into the brain along a predefined trajectory; wherein steps of applying the stimulus, detecting a resonant response and determining one or more waveform characteristics of the detected resonant response are repeated while the at least one electrode is being inserted to generate a profile of resonant responses with respect to the predefined trajectory and the target neural structure.

The profile of resonant responses may be used to determine a position of the one or more electrodes relative to the target neural structure.

The at least one electrode may comprises a plurality of electrodes, and the steps of applying the stimulus, detecting a resonant response and determining one or more waveform characteristics of the detected resonant response may be repeated using different combinations of the at least one electrode to generate a profile of resonant responses.

The method may further comprise: selecting one or more of the at least one electrode based on the profile of neural responses; and applying a therapeutic stimulus to the selected one or more of the at least one electrode. The selected one or more of the at least one electrode may comprise a plurality of electrodes.

The one or more of the at least one electrode used to apply the stimulus may comprise at least two electrodes. Equally, the one or more of the at least one electrode used to detect the resonant response may comprise at least two electrodes.

The neural target structure may be part of the cortico-basal ganglia-thalamocortical circuit.

The neural target structure may be the subthalamic nucleus, globus pallidus interna, substantia nigra pars reticulata, pedunculopontine nucleus.

According to a second aspect of the disclosure, there is provided a neurostimulation system, comprising: a lead having at least one electrode adapted for implantation in or near a target neural structure in the brain; a signal generator selectively coupled to one or more of the at least one electrode and configured to generate a stimulus to stimulate the target neural structure; a measurement device selectively coupled to one or more of the at least one electrode and configured to detect a resonant response from the target neural structure evoked by the stimulus; a processing unit coupled to the measurement device and configured to determine one or more waveform characteristics of the detected resonant response.

The one or more waveform characteristics may be determined based on at least part of a second or subsequent cycle in the detected resonant response.

The one or more waveform characteristics comprises one or more of the following: a) a frequency of the resonant response; b) a temporal envelope of the resonant response; c) an amplitude of the resonant response; d) a fine structure of the resonant response; e) a rate of decay of the resonant response; f) a delay between the onset of the stimulus and the onset of a temporal feature of the resonant response.

The stimulus may comprise a plurality of pulses.

In determining the one or more waveform characteristics, the processing unit may be configured to correlate a first characteristic over two or more cycles of the detected resonant response.

In determining the one or more waveform characteristics, the processing unit may be configured to determine a degree of change of the first characteristic over the two or more cycles.

In determining the one or more waveform characteristics, the processing unit may be configured to determine a rate of change of the first characteristic over the two or more cycles.

The resonant response may be detected at a different one or more electrodes to the one or more electrodes at which the stimulus is applied.

The resonant response may comprise a plurality of resonant components.

The processing unit may be coupled to the signal generator and configured to selectively control the output of the signal generator.

The processing unit may be configured to: control the signal generator to adapt the stimulus based on the one or more determined waveform characteristics of the resonant response.

The processing unit may be further configured to: correlate the detected resonant response with a template resonant response; and control the signal generator to adapt the stimulus based on the correlation.

The processing unit may be configured to: correlate the one or more determined waveform characteristics with one or more predetermined threshold values; and control the signal generator to adapt the stimulus based on the correlation.

The adapting may comprise adjusting one or more of the frequency, amplitude, pulse-width, electrode configuration, or morphology of the stimulus.

The stimulus may be non-therapeutic or therapeutic.

The stimulus may comprise a patterned signal comprising a plurality of bursts separated by a first time period, each burst comprising a plurality of pulses separated by a second time period, wherein the first time period is greater than the second time period and wherein the detecting is performed during one or more of the first time periods. The first time period is greater than or equal to the second time period. The plurality of pulses within at least one of the bursts may have different amplitudes.

The different amplitudes may be selected to produce a ramp in amplitude of sequential pulses in the at least one of the bursts.

The final pulse in each of the plurality of bursts is preferably substantially identical.

The processing unit may be configured to: estimate a patient state of a patient based on the determined one or more waveform characteristics.

The processing unit may be configured to: diagnosing the patient based on the estimate of the patient's state.

The processing unit may be configured to: generating one or more alerts associated with the estimated patient state; and output the one or more alerts.

The processing unit may be configured to: estimate a degree of progression of a disease associated with the patient or an effect of a therapy provided to the patient based on the one or more waveform characteristics and one or more second waveform characteristics, the one or more second waveform characteristics determined based on a second resonant response detected after the resonant response.

The therapy may be medication or deep brain stimulation.

The system may further comprise: a second lead having at least one second electrode adapted for implantation in or near a second target structure in the brain; wherein the signal generator is selectively coupled to one or more of the at least one second electrode and configured to generate a stimulus to stimulate the second target neural structure; wherein the measurement device is selectively coupled to one or more of the at least one second electrode and configured to detect a resonant response from the second target neural structure evoked by the stimulus; a processing unit coupled to the measurement device and configured to determine one or more waveform characteristics of the detected resonant response from the second target neural structure.

The lead and the second lead may be located within or near to different neural structures in the brain. The lead and the second lead may be located within different hemispheres of the brain.

The processing unit may be configured to: determine whether one or more of the at least one electrode is positioned in the target neural network based on the detected resonant response.

The signal generator, the measurement device and the processing unit are may be configured to repeat the steps of applying the stimulus, detecting a resonant response and determining one or more waveform characteristics of the detected resonant response. In which case, the steps of applying the stimulus, detecting a resonant response and determining one or more waveform characteristics of the detected resonant response may be repeated until processing unit determines that one or more of the at least one electrode is positioned in the target neural structure.

The processing unit may be configured to control the signal generator to: select one or more of the at least one electrode to use for therapeutic stimulation of the target neural structure based on the one or more waveform characteristics; and apply a therapeutic stimulus to the target neural structure via the selected one or more of the at least one electrode.

The steps of applying the stimulus, detecting a resonant response and determining one or more waveform characteristics of the detected resonant response may be repeated while the at least one electrode is being inserted; and the processing unit may be further configured to generate a profile of resonant responses with respect to the predefined trajectory and the target neural structure.

The processing unit may be configured to determine a position of the one or more electrodes relative to the target neural structure based on the profile of resonant responses.

The at least one electrode may comprise a plurality of electrodes. In which case, the steps of applying the stimulus, detecting a resonant response and determining one or more waveform characteristics of the detected resonant response may be repeated using different combinations of the at least one electrode to generate a profile of resonant responses.

The processing unit may be configured to: select one or more of the at least one electrode based on the profile of neural responses; and control the signal generator to applying a therapeutic stimulus to the selected one or more of the at least one electrode.

The selected one or more of the at least one electrode may comprise a plurality of electrodes.

The one or more of the at least one electrode used to apply the stimulus may comprise at least two electrodes and/or wherein the one or more of the at least one electrode used to detect the resonant response comprises at least two electrodes.

The neural target structure may be part of the cortico-basal ganglia-thalamocortical circuit.

The neural target structure may be the subthalamic nucleus, globus pallidus interna, substantia nigra pars reticulata, pedunculopontine nucleus.

According to a third aspect of the disclosure, there is provided a method of monitoring neural activity in a brain responsive to an stimulus, the method comprising: a. applying the stimulus to a target neural structure in the brain; and b. detecting a neural response evoked by the stimulus at an electrode implanted in or near the target neural structure, wherein the stimulus comprises a patterned signal comprising a plurality of bursts separated by a first time period, each burst comprising a plurality of pulses separated by a second time period, wherein the first time period is greater than the second time period and wherein the detecting is performed during one or more of the first time periods.

The first time period is preferably greater than or equal to the second time period.

The stimulus is preferably biphasic. The plurality of pulses within a burst may have different amplitudes. The different amplitudes may be selected to produce a ramp. The final pulse in each of the plurality of bursts may be substantially identical. The stimulus may be patterned to be non-therapeutic or therapeutic.

BRIEF DESCRIPTION OF DRAWINGS

Embodiments of the present disclosure will now be described by way of non-limiting examples with reference to the drawings, in which.

DESCRIPTION OF EMBODIMENTS

Embodiments of the present disclosure relate to improvements in neuro-stimulation in the brain. DBS devices typically apply a constant amplitude stimulus to a target area of the brain at a constant frequency of 130 Hz. The inventors have determined not only that application of such a stimulus evokes a neural response from the target area of the brain, but that the neural response comprises a resonant component which has not previously been recognised. Continuous DBS at conventional frequencies does not allow a long enough time window to observe the resonant activity. However, by monitoring the neural response after stimulation has ceased (by patterning the stimulation signal or otherwise), the resonant activity can be monitored. In addition, the inventors have realised that embodiments of the present invention have applications both for reducing the physical effects associated with motor diseases, and also the detrimental effects of other neurological conditions, neuropsychiatric disorders, sensory disorders, and pain.

Figure 1:
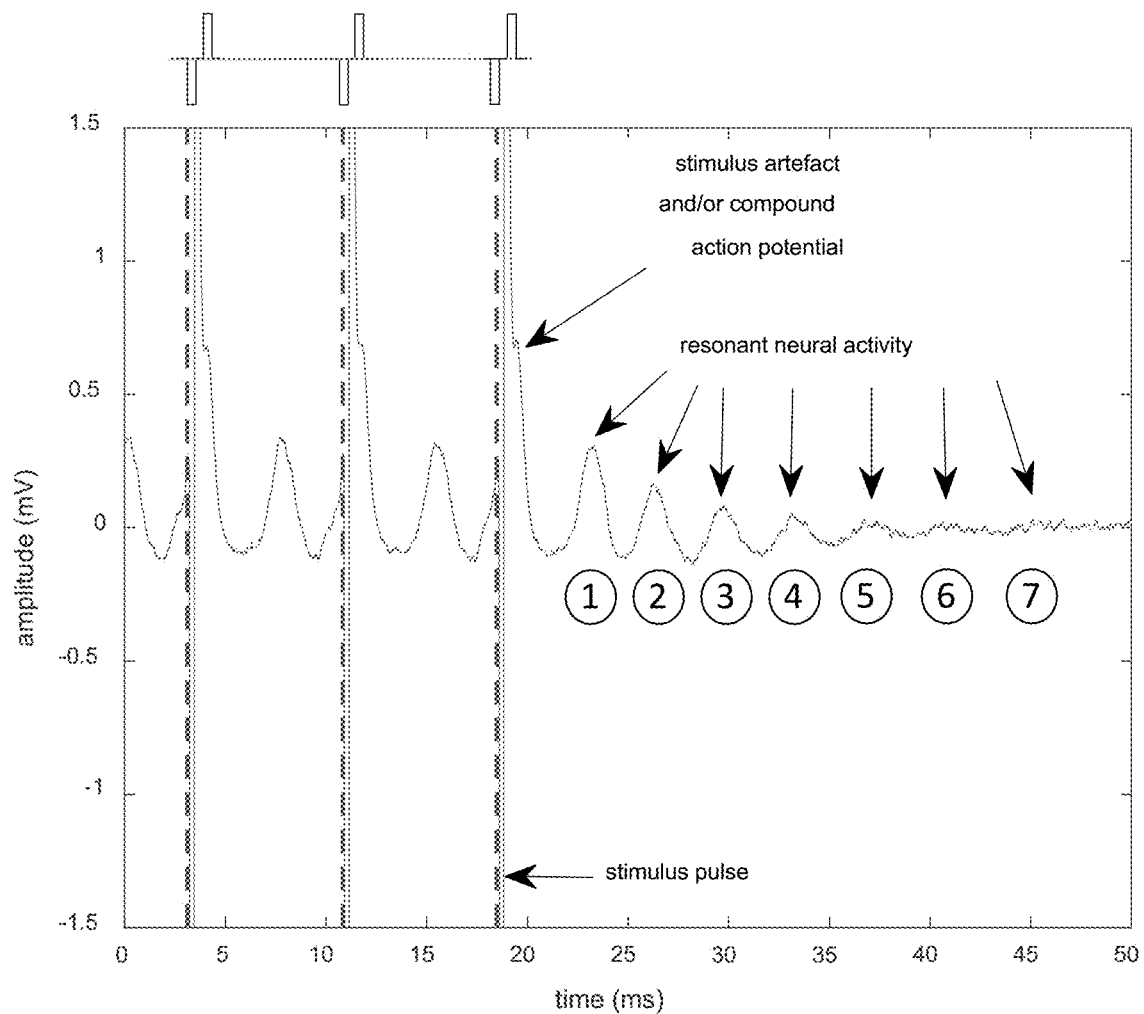
FIG. 1 is a graph illustrating resonance from a neural structure responsive to a deep brain stimulation (DBS) signal.

In addition to the above, the inventors have also realised that neuronal oscillations, as reflected in local field potentials measured, for example, via implanted electrodes, by EEG, or by MEG, are also affected both by DBS and certain medications used to treat movement disorders. In particular, high frequency oscillations (HFOs) in the range of 200 to 400 Hz, measured in local field potentials by DBS electrodes implanted in the subthalamic nucleus (STN) of the brain, have been found to be modulated both by DBS and with the use of medication, such as levodopa. This realisation has led the inventors to develop novel techniques of selecting optimal DBS treatment parameters based on measured HFO modulation. FIG. 1 graphically illustrates a response from a neural circuit stimulated by a 130 Hz signal delivered from a neurostimulator via an electrode lead, such as the 3387 electrode lead manufactured by Medtronic®, implanted in the subthalamic nucleus (STN) of a Parkinson's disease (PD) patient. Each response to a stimulus pulse comprises an evoked compound action potential (ECAP) component together with a component of evoked resonant neural activity (ERNA) occurring after the ECAP. The ECAP typically occurs within 1-2 milliseconds of the stimulus pulse. The graph shows the response to the last three consecutive pulses of a 60 second period of continuous stimulation followed by a period of no stimulation. It can be seen that the evoked resonant response to each of the first two stimulus pulses shown in FIG. 1 is cut short by the onset of the next stimulus pulse, such that only a single secondary peak is detected. However, the evoked resonant response to the third (and final) pulse is able to resonate for longer and so can be clearly seen in the form of a decaying oscillation with at least seven peaks for a post-stimulus period of about 30 milliseconds.

As mentioned above, it is known for clinicians to control and adjust DBS parameters to elicit therapeutic effects in a patient. The inventors have realised that by controlling the DBS parameters in certain ways, a non-therapeutic stimulus can be administered which evokes a resonant neural response (ERNA) in a patient without having any therapeutic impact or causing undesirable side effects. Such non-therapeutic stimuli can be used to reliably measure ERNA without causing sustained changes to the resonant neural circuit or the patient's symptomatic state. Non-therapeutic stimulation is preferably achieved by administering a stimulus comprising a short burst of pulses followed by a period of no stimulation, and the ERNA is measured during this period of no stimulation. By doing so, the total charge or energy provided to the patient is below a therapeutic threshold, and the measured ERNA provides information concerning the patient's natural state (without therapy). In an alternative embodiment, the overall charge or energy provided to the patient may be reduced by reducing the amplitude of the stimulation signal below a therapeutic threshold. However, doing so may also reduce the amplitude of peaks in the ERNA making it more difficult to observe.

In addition to the above, the inventors have determined that patterned stimulation can be used to monitor and analyse evoked resonant neural activity during therapeutic stimulation of a patient. By patterning the stimulation signal, therapeutic stimulation can be maintained whilst providing time windows in which to monitor resonant responses past that of the first resonant peak or more preferably past two or more resonant peaks.

Figure 2:
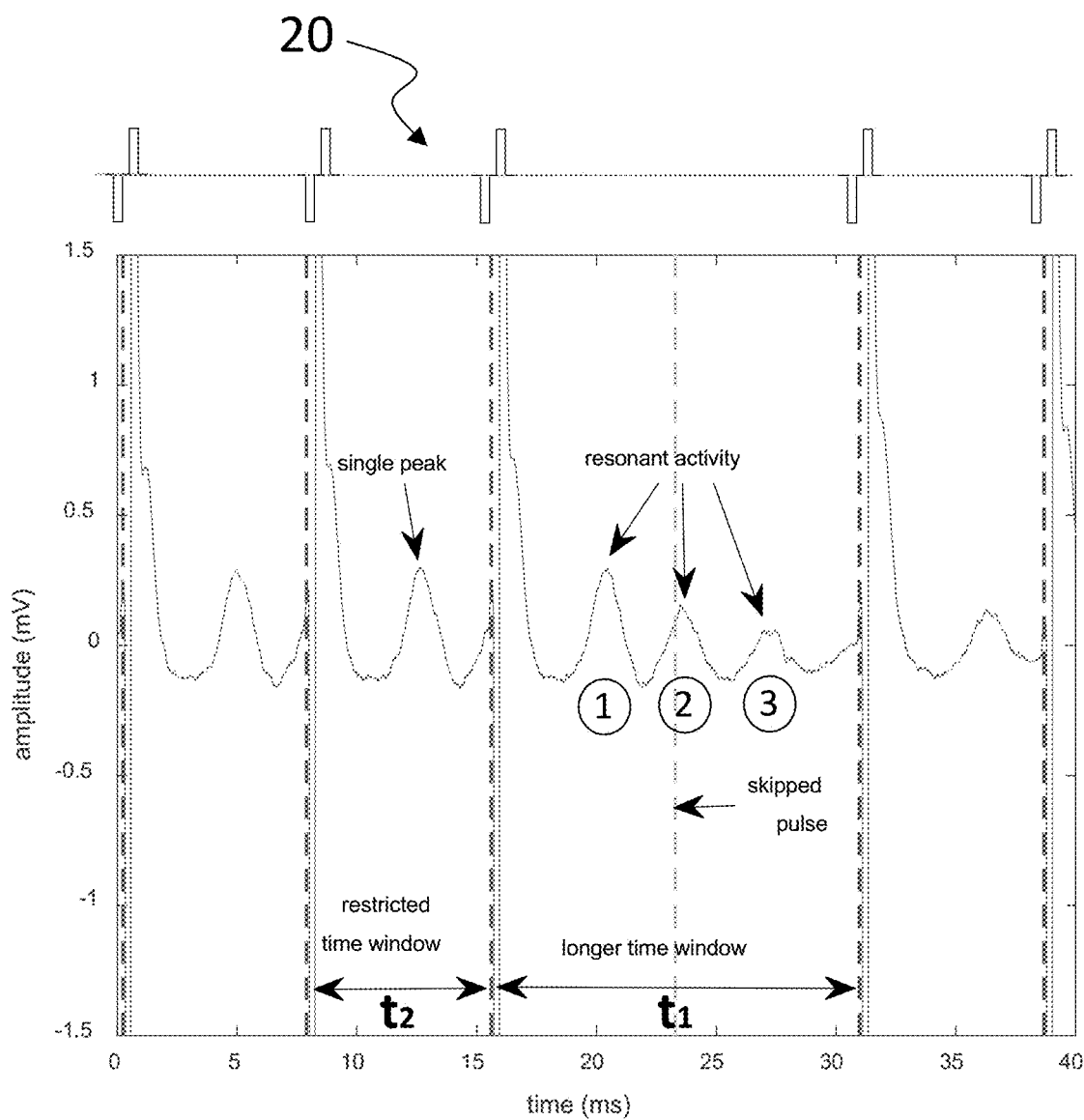
FIG. 2 is a graph illustrating resonance from a neural structure responsive to a patterned DBS signal.

FIG. 2 graphically illustrates an example therapeutic patterned DBS stimulus 20 and the associated evoked resonant response according to an embodiment of the present disclosure. The patterned stimulus 20 is shown above the graph to illustrate the correlation between stimulus and response. In the patterned stimulus, a single pulse has been omitted from an otherwise continuous 130 Hz pulse train. The pulse train therefore includes a plurality of bursts of pulses of continuous stimulation, each burst separated by a first time period $t_1$, each of the plurality of pulses separated by a second time period $t_2$. Continuation of the stimulus before and after omission of a pulse (or more than one pulse) maintains the therapeutic nature of the DBS, whilst the omission of a pulse allows for resonance of the ERNA to be monitored over several (3 in this example) resonant cycles before the next stimulation pulse interrupts this resonance.

In summary, by patterning non-therapeutic and therapeutic stimuli, an evoked response can be monitored over a longer period of time than with conventional non-patterned stimulation. Accordingly, stimuli are preferably applied in bursts of multiple pulses, each burst separated by a first time period $t_1$ of no stimulation, each pulse separated by a second time period $t_2$. For example, a stimulus signal may comprise a series of 10-pulse bursts at 130 Hz. To increase repeatability of results, the multi-pulse burst may be repeated after a predetermined period of no stimulation. For example, the multi-pulse burst may be repeated each second. The duration of the first time period $t_1$ is greater than that of the second time period $t_2$. The ratio between the duration of the burst and the duration between bursts may be chosen so as to ensure that relevant properties of the ERNA can be monitored easily and efficiently. In some embodiments, the duration of each burst is chosen to be between 1% and 20% of the duration of no stimulation between bursts.

Figure 3:
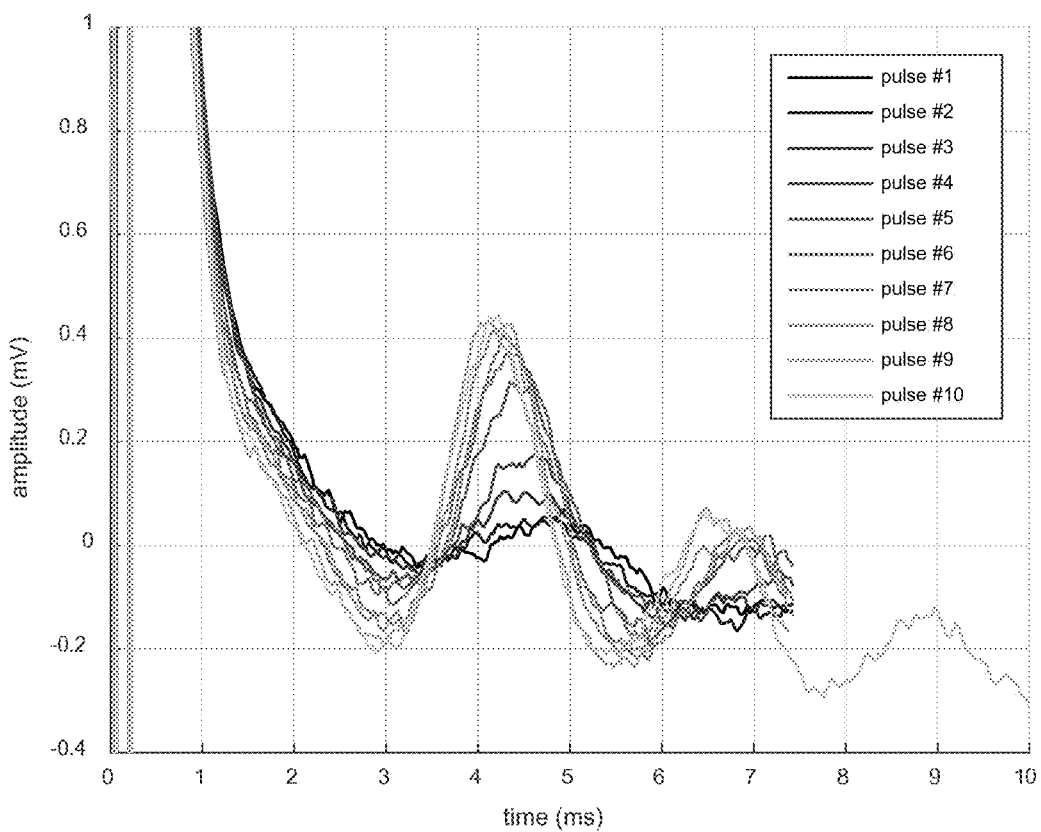
FIG. 3 is a graph illustrating evoked resonance responsive to 10 consecutive pulses of a DBS signal.

In other embodiments, the duration of each burst may be chosen to minimise the effects of stimulation on the measured ERNA or to accentuate particular features of the measured ERNA. FIG. 3 graphically illustrates how the application of 10 pulses at 130 Hz can affect ERNA. The response to the first pulse has a broad, low amplitude first peak. The first peak becomes larger and sharper for subsequent pulses, whilst also shifting to an earlier time. In some embodiments, the optimum number of pulses comprised in a burst may be chosen to maximise the amplitude of the resonance, whilst minimizing the time shift of a peak in ERNA across the burst (e.g, the fourth pulse). In other embodiments, the rate of change in ERNA features (e.g. amplitude, onset delay) across consecutive pulses in a burst may be used as a defining characteristic. For example the rate of change across a burst may be used to determine electrode position, optimum parameters, patient state, etc. and/or as a closed loop control signal.

Figure 4:
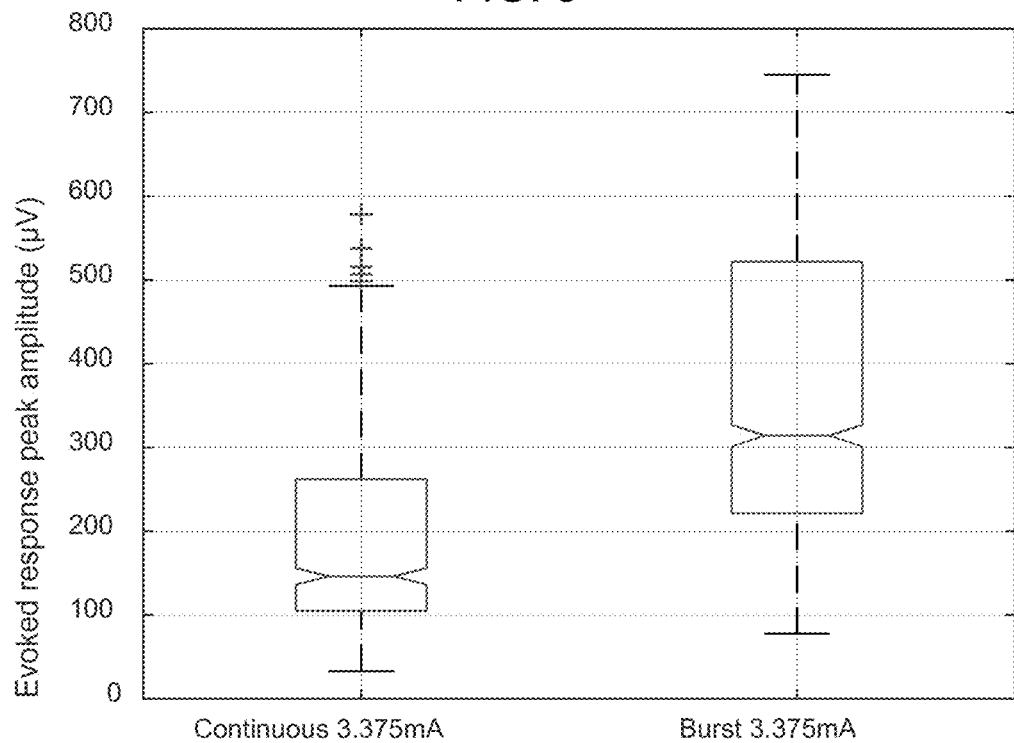
FIG. 4 is a graph illustrating the range and variance of peak amplitude of a resonant response to continuous and patterned DBS.

The use of bursts (e.g. 10 pulses) stimulation provides high amplitude evoked neural responses, making them easier to measure than responses to more continuous DBS. FIG. 4 graphically illustrates the range and variance of first peak amplitude of ERNA responsive to more continuous DBS where one pulse is skipped every second (left) and burst DBS (right) (10 pulses only per second). It can be seen that the average peak amplitude of ERNA responsive to burst DBS is around 310 μV whereas the average peak amplitude of ERNA responsive to more continuous DBS is around 140 μV. Further, by using burst stimulation, the evoked resonant response over several oscillatory cycles (20 milliseconds or more) can be monitored.

By analysing characteristics of the ERNA, the inventors have determined that waveform characteristics of the ERNA (natural frequency, damping factor, envelope, fine structure, onset delay, rate of change, etc.) are dependent on various physiological conditions of the patient. For example, it has been found that therapeutic DBS decreases the frequency of resonance of the target neural circuit.

Changes in ERNA Related to DBS Stimulation

Figures 5A, 5B, 5C:
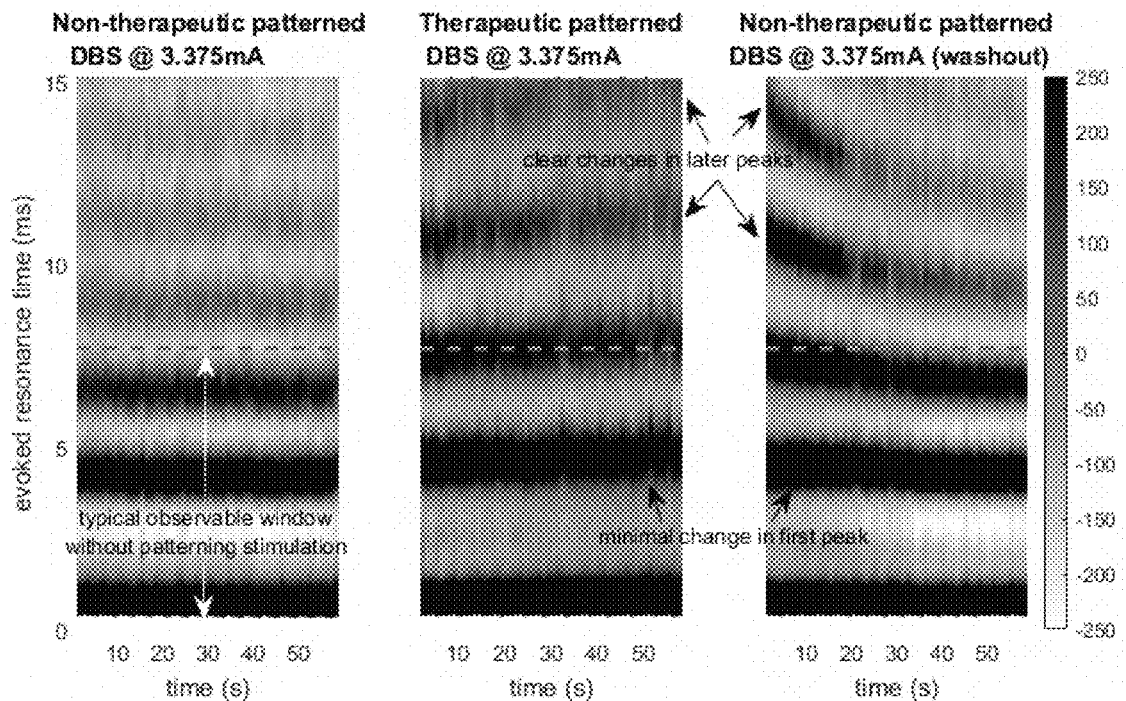
FIG. 5A is a graphical illustration showing neural resonance evoked by a continuous non-therapeutic patterned DBS signal.
FIG. 5B is a graphical illustration showing neural resonance evoked by a continuous therapeutic patterned DBS signal.
FIG. 5C is a graphical illustration showing neural resonance after a transition from a continuous therapeutic DBS signal to a non-therapeutic DBS signal.

FIGS. 5A, 5B, and 5C illustrate the variation of frequency of the ERNA during non-therapeutic stimulation (FIG. 5A), therapeutic stimulation (FIG. 5B), and the ERNA after a transition of stimulation from therapeutic stimulation to non-therapeutic stimulation (FIG. 5C). Resonant frequency of the ERNA was measured by calculating the inverse of the time delay between the maxima of two peaks of the ERNA. In other embodiments, the resonant frequency may be calculated as an inverse of the average time delay between maxima of all detected peaks of the ERNA. In further embodiments, the resonant frequency may be calculated by fitting a damped oscillator model to the resonant activity and extracting the natural frequency or by performing spectral analyses (e.g. Fourier transform, wavelet transform). Other techniques for frequency estimation, such as estimating the time between zero-crossings in the waveform or using other features of the waveform may also be used for this purpose.

In the example shown, a patterned stimulus was administered to the patient in the same manner as described with reference to FIGS. 1 and 2. FIGS. 5A and 5B show the responses to a patterned non-therapeutic and therapeutic DBS stimulation, respectively. In this example, non-therapeutic stimulation consisted of bursts of 10 pulses delivered at a frequency of 130 Hz over a 1-second time period with the remaining 120 pulses (which would be present during continuous stimulation) skipped. The typical observable window of the response (during continuous (non-patterned) DBS) is denoted by the horizontal dotted line. It can be seen that with patterned non-therapeutic stimulation, the amplitude and frequency of the ERNA remain relatively constant indicating that the stimulus did not strongly affect the resonant state of the target neural structure over time. Further, two resonant peaks of the ERNA (represented in black) can be seen in the typical observable window for non-patterned stimulation. FIG. 5B then shows the responses to therapeutic patterned DBS stimulation at 3.375 mA where 129 pulses are delivered per second at a rate of 130 Hz, with the remaining 1 pulse skipped.

The therapeutic signal causes the frequency of the ERNA to reduce, in turn potentially causing the second resonant peak of the ERNA to move outside the typical observable window for continuous (non-patterned) stimulation. However by patterning the stimulation by skipping one or more pulses, it is possible to continue to measure the resonant properties of the ERNA, along with subsequent peaks during the period in which a stimulation pulse is omitted. Additionally, it can be seen that the amplitude of the third and fourth resonant peaks are increased in comparison to the non-therapeutic responses.

Alternative methods of patterning the stimulation, rather than merely omitting pulses in a periodic pulse train, may improve the monitoring of ERNA. For example, conventional, therapeutic stimulation (e.g. at a frequency of 130 Hz) may be interleaved with bursts of stimulation having a lower frequency (e.g. 90 Hz). The frequency of these interleaving bursts is preferably low enough to allow for multiple ERNA peaks to be observed. Equally, the frequency of these interleaving bursts is preferably high enough to be within the therapeutic frequency range for DBS. The transition between frequency may be abrupt or, alternatively the change in frequency may be gradual. Applying ramps to the frequency of the pulses to avoid an abrupt step change in frequency may be advantageous.

Additionally or alternatively to adjusting the frequency of the applied stimulus, the amplitude of pulses may be modulated over time. This may include applying a ramp to increase the pulse amplitudes over several pulses within a burst and/or a ramp to decrease the pulse amplitudes over several pulses within a burst. To enhance the monitoring of ERNA it may be advantageous to apply a fixed amplitude to the pulses preceding the observation window, and if this amplitude differs from that applied at other times (e.g. to maximise therapeutic benefit), then applying ramps to the amplitude of the pulses to avoid an abrupt step change in amplitude may be advantageous.

FIG. 5C then shows the responses after switching back to the non-therapeutic patterned stimulation. In this case the therapeutic effect of the patterned therapeutic stimulus 'washes out' and the ERNA returns to its baseline state. It can be seen that the first peak of resonant activity across all conditions (typically all that can be measured using conventional continuous DBS) does not vary greatly with therapeutic DBS. However, characteristics of subsequent parts of the ERNA waveform, made measurable by patterning the stimulation, exhibit much larger changes in frequency and amplitude. Monitoring of the response over a longer period therefore enables information concerning frequency, amplitude, envelope, and fine structure of the time-varying oscillation to be analysed.

Figures 5D, 5E, 5F:
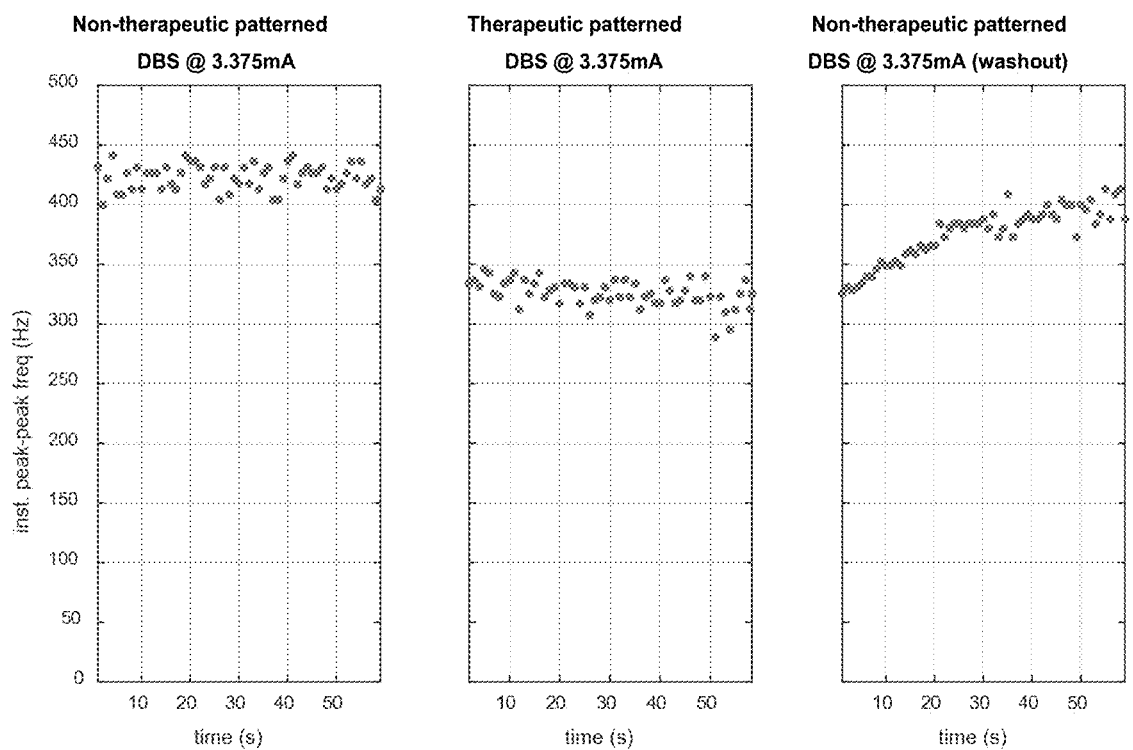
FIG. 5D is a graph illustrating the estimated frequency of evoked resonance responsive to a non-therapeutic DBS signal.
FIG. 5E is a graph illustrating the estimated frequency of evoked resonance responsive to a therapeutic DBS signal.
FIG. 5F is a graph illustrating the estimated frequency of evoked resonance responsive to a transition between a therapeutic DBS signal and a non-therapeutic DBS signal.

This effect is further illustrated by FIGS. 5D, 5E, and 5F. FIG. 5D shows the resonant frequency of the ERNA during periods of non-therapeutic stimulation to be around 400-450 Hz. Clinically effective stimulation (stimulation operable to actively reduce a patient's disease symptoms) reduces the frequency of the ERNA to around 300-350 Hz as shown in FIG. 5E. FIG. 5F illustrates the transition of resonant frequency from 300-350 Hz back to around 400-450 Hz after therapeutic stimulation has been replaced with non-therapeutic stimulation.

Figures 6A, 6B, 6C:
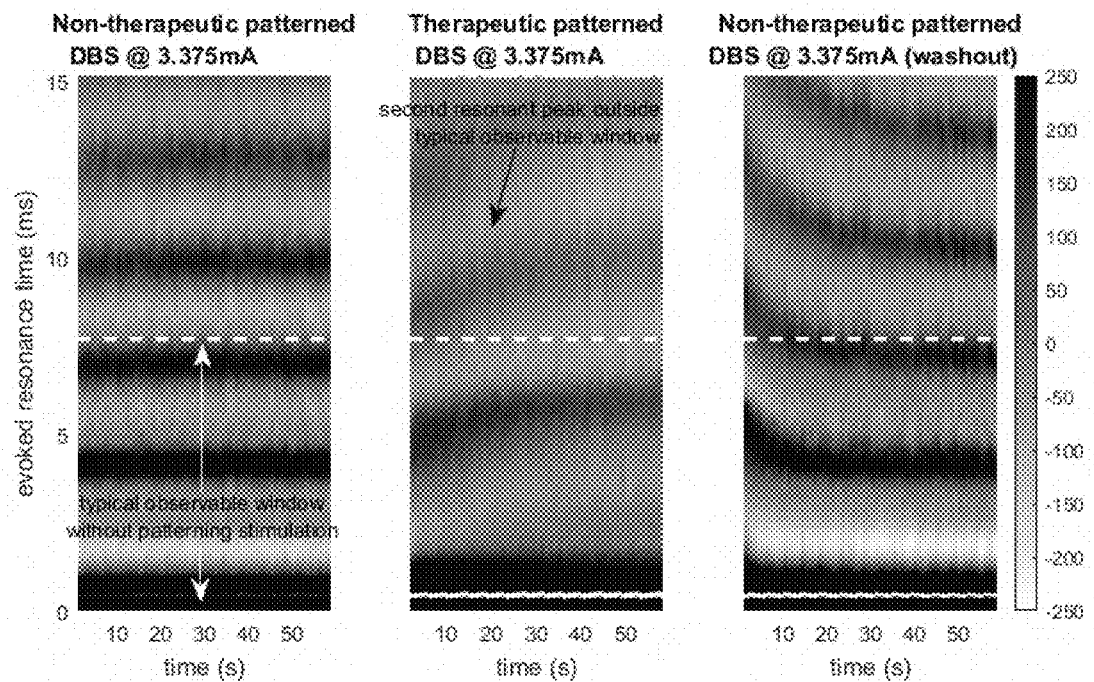
FIG. 6A is a graphical illustration showing neural resonance evoked by a continuous non-therapeutic patterned DBS signal.
FIG. 6B is a graphical illustration showing neural resonance evoked by a continuous therapeutic patterned DBS signal.
FIG. 6C is a graphical illustration showing neural resonance after a transition from a continuous therapeutic DBS signal to a non-therapeutic DBS signal.

FIGS. 6A, 6B, and 6C illustrate another example from a different patient of the variation of the ERNA during non-therapeutic patterned stimulation (FIG. 6A), therapeutic patterned stimulation (FIG. 6B) and the ERNA after a transition from therapeutic stimulation to non-therapeutic stimulation (FIG. 6C). In this example, patterned stimuli were administered to the patient in the same manner as described with reference to FIGS. 5A to 5E. As with the previous example, it can be seen that the initial non-therapeutic stimulation (FIG. 6A) does not cause noticeable changes to the ERNA and that the therapeutic stimulation (FIG. 6B) causes a reduction in the frequency of the resonance, which returns to baseline levels after the stimuli is transitioned back to non-therapeutic patterned stimulation (FIG. 6C). However, in this example, the change in resonant frequency with therapeutic stimulation is accompanied by an increase in the delay between each stimulus pulse and the onset of the resonance. This increase in onset delay shifts the second resonant peak such that it occurs outside the typical observable window for conventional (non-patterned) DBS. By patterning the stimulation, the measurement window is made long enough to observe three resonant peaks, allowing ERNA to be characterised. Furthermore, contrary to the previous example, the amplitude of the resonance is decreased by therapeutic stimulation.

Figures 6D, 6E, 6F:
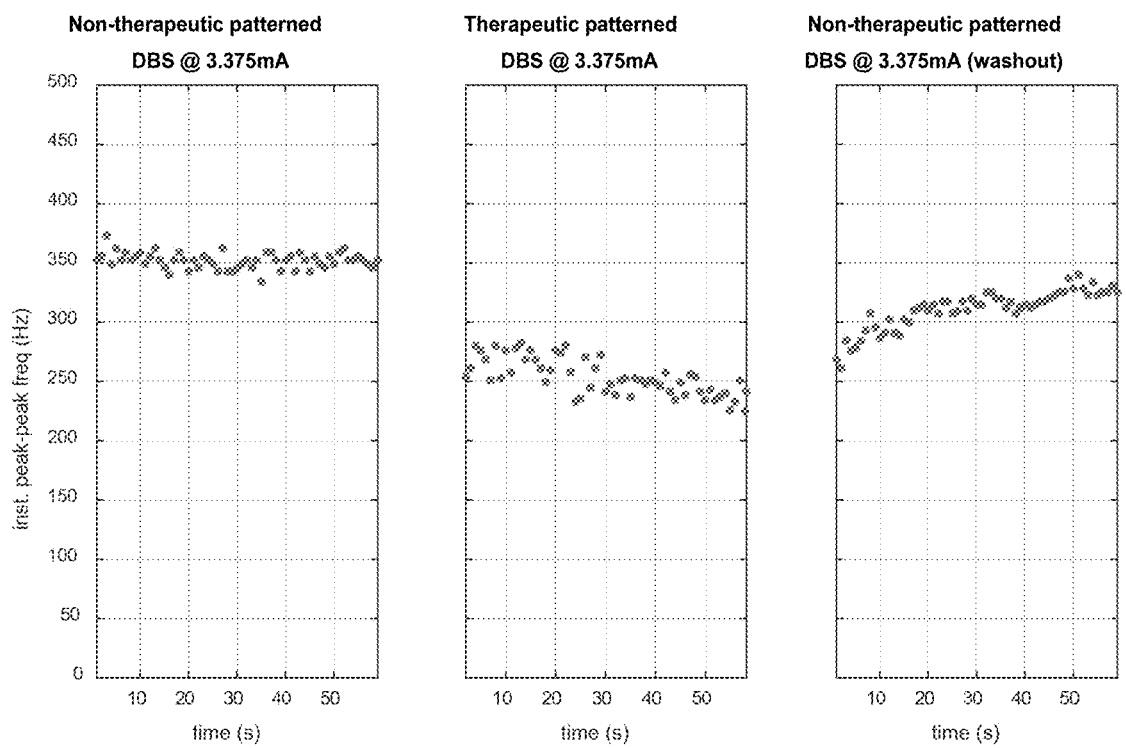
FIG. 6D is a graph illustrating the estimated frequency of evoked resonance responsive to a non-therapeutic DBS signal.
FIG. 6E is a graph illustrating the estimated frequency of evoked resonance responsive to a therapeutic DBS signal.
FIG. 6F is a graph illustrating the estimated frequency of evoked resonance responsive to a transition between a therapeutic DBS signal and a non-therapeutic DBS signal.

FIGS. 6D, 6E, and 6F further illustrate the reduction in resonant frequency with therapeutic stimulation in this example. Resonant frequency was estimated by calculating the inverse of the time delay between the maxima of two peaks of the ERNA. In FIG. 6D, the frequency of the ERNA measured using non-therapeutic patterned stimulation can be seen to be about 350 Hz. The application of therapeutic patterned stimulation in FIG. 6E causes the frequency to decrease to around 250 Hz. The frequency can be seen to be returning to its baseline level in FIG. 6F after transitioning back to non-therapeutic patterned stimulation.

ERNA Comprising Multiple Resonances

Figures 7A, 7B, 7C:
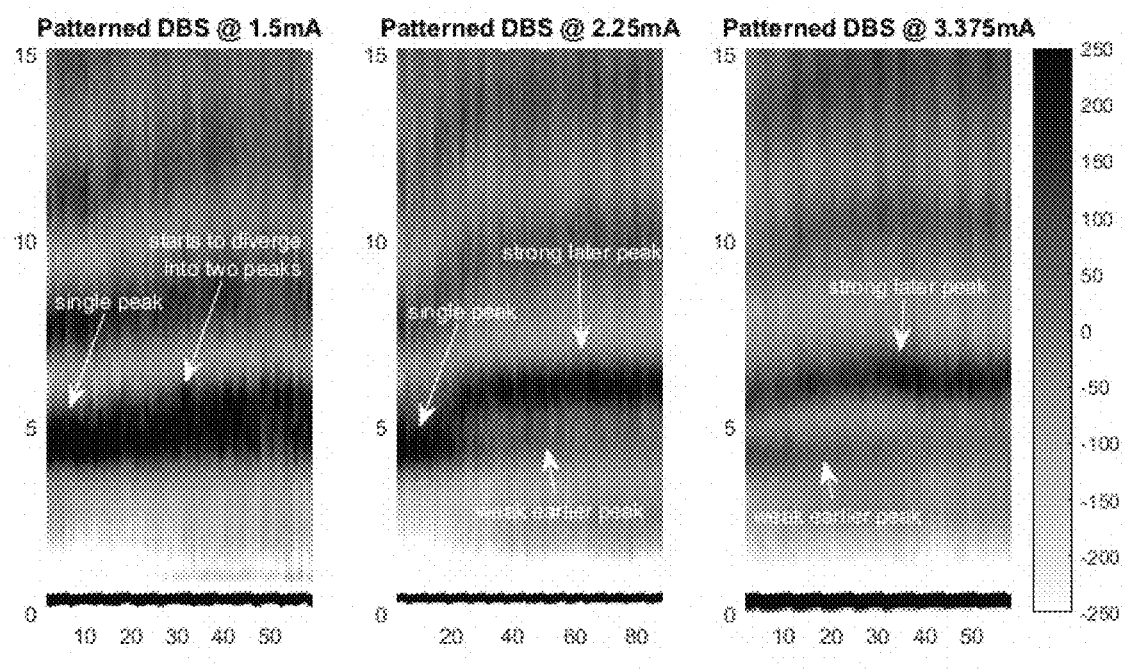
FIG. 7A is a graph illustrating evoked resonances beginning to diverge into two peaks in response to patterned DBS with an amplitude of 1.5 mA.
FIG. 7B is a graph illustrating evoked resonances diverging into two peaks in response to patterned DBS with an amplitude of 2.25 mA.
FIG. 7C is a graph illustrating two separate evoked resonant peaks in response to patterned DBS with an amplitude of 3.375 mA.

The inventors have determined not only that evoked neural responses to applied stimuli exhibit resonant activity, but that in some instances evoked activity comprises multiple resonances. FIGS. 7A, 7B and 7C illustrates ERNA in response to continuous DBS at 1.5 mA, 2.25 mA and 3.375 mA respectively. At 1.5 mA the resonant ERNA starts as a single peak, which can be seen to begin to diverge slightly into two peaks. At 2.25 mA, the dominance switches to the later of the two peaks. However, the earlier peak, which was dominant at 1.5 mA, continues at a lower amplitude. At 3.375 mA, two peaks are present, with the later peak dominating. It is thought that these multiple resonant peaks correspond to activity in different neural circuits. The relative amplitude between these resonant responses (or other features, such as temporal or spectral properties) may be an indicator of therapeutic state.

ERNA Measurements from Chronically Implanted Electrodes

FIGS. 20 to 23C provide further evidence of the positive effects of DBS on patient symptoms and related changes in ERNA. The data shown in these figures was collected from a patient with Parkinson's disease implanted with an electrode array. The electrode array was implanted chronically, and measurements of ERNA and movement state were made several months after implantation. By measuring ERNA and movement state at this time, it could be presumed that the electrode array and its neural environment were stable. Accordingly, the confirmed relationship between ERNA and movement state is more representative of the long-term condition of a patient than those relationships measured during acute intraoperative procedures, or studies conducted within a few days of electrode insertion. It has been found that findings from such short-term studies may be confounded by a 'stun effect' that is characterised by temporary alleviation of motor deficits in Parkinson's disease presumably related to the surgical implantation procedure rather than application of therapeutic DBS itself.

ERNA measurements were collected in a similar manner to that described above with reference to FIGS. 5A to 6F. Measurements of the patient's movement functions were also collected. These included estimates of muscle rigidity, speed of finger tapping, and facility of opening and closing the hand.

DBS at different stimulation amplitudes was applied to the implanted electrode array in a similar manner to that described above. Stimulation amplitudes included zero, 0.667 mA, 1 mA, 1.5 mA, 2.25 mA and 3.375 mA. Non-therapeutic burst stimuli were also provided before and after the periods of conventional DBS.

Figure 20:
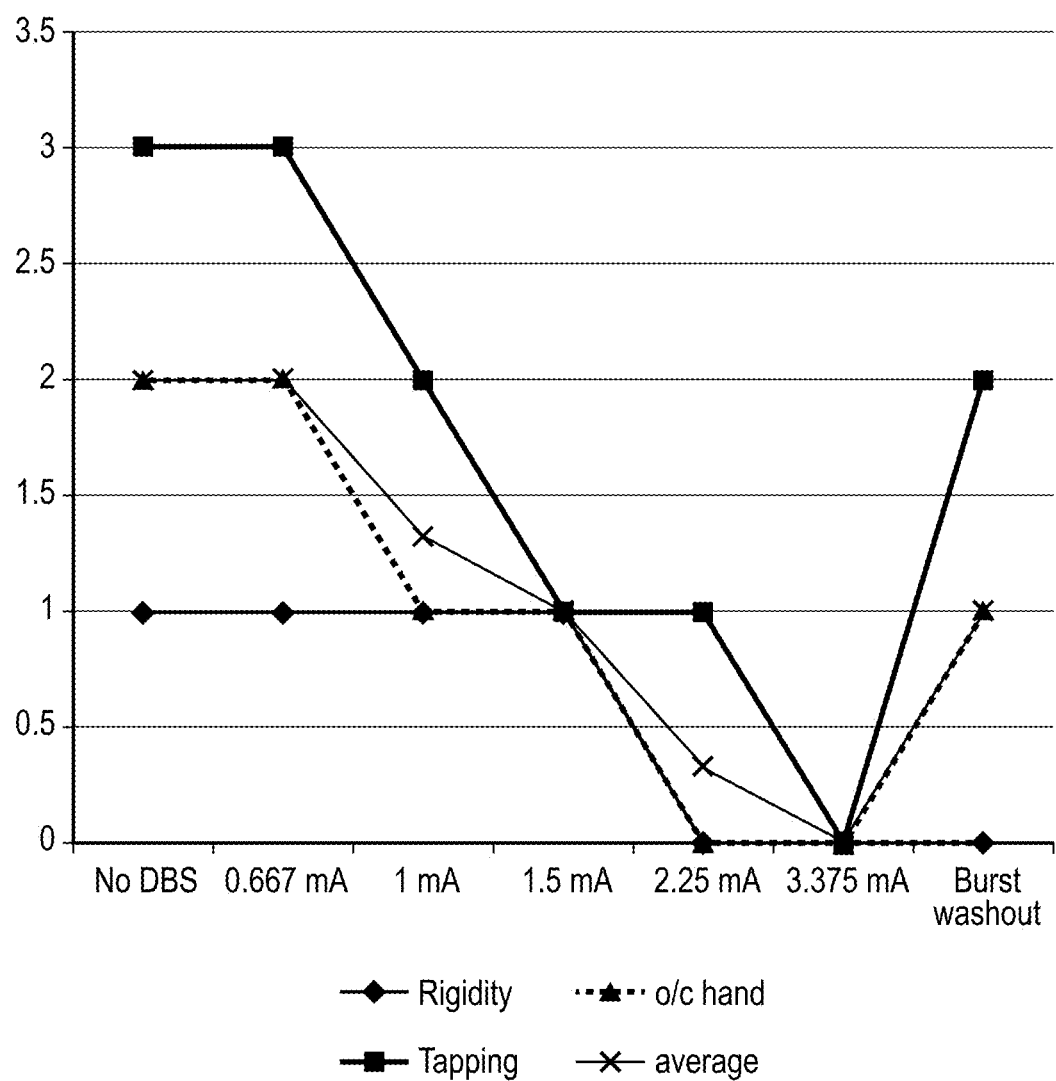
FIG. 20 illustrates the results of movement function tests for patients receiving DBS.

FIG. 20 graphically illustrates the results of the movement function tests. The observations of rigidity, finger tapping and opening/closing of the patient's hand are shown separately, with the average of those measures shown in bold. The observations of patient impairment were scored from 0 (zero) to 4 where 4 indicated the most impairment and zero indicated the least (or no) movement. This scale is provided on the vertical axis of FIG. 20.

It is evident from FIG. 20 that DBS improved all movement scores, with the average score showing a marked benefit, particularly at the highest levels of DBS (2.25 mA and 3.375 mA). Patient movement began to return to pre-DBS conditions during the final burst washout period, during which stimulation parameters were selected so as to produce no therapeutic effect.

Figures 21A, 21B, 21C:
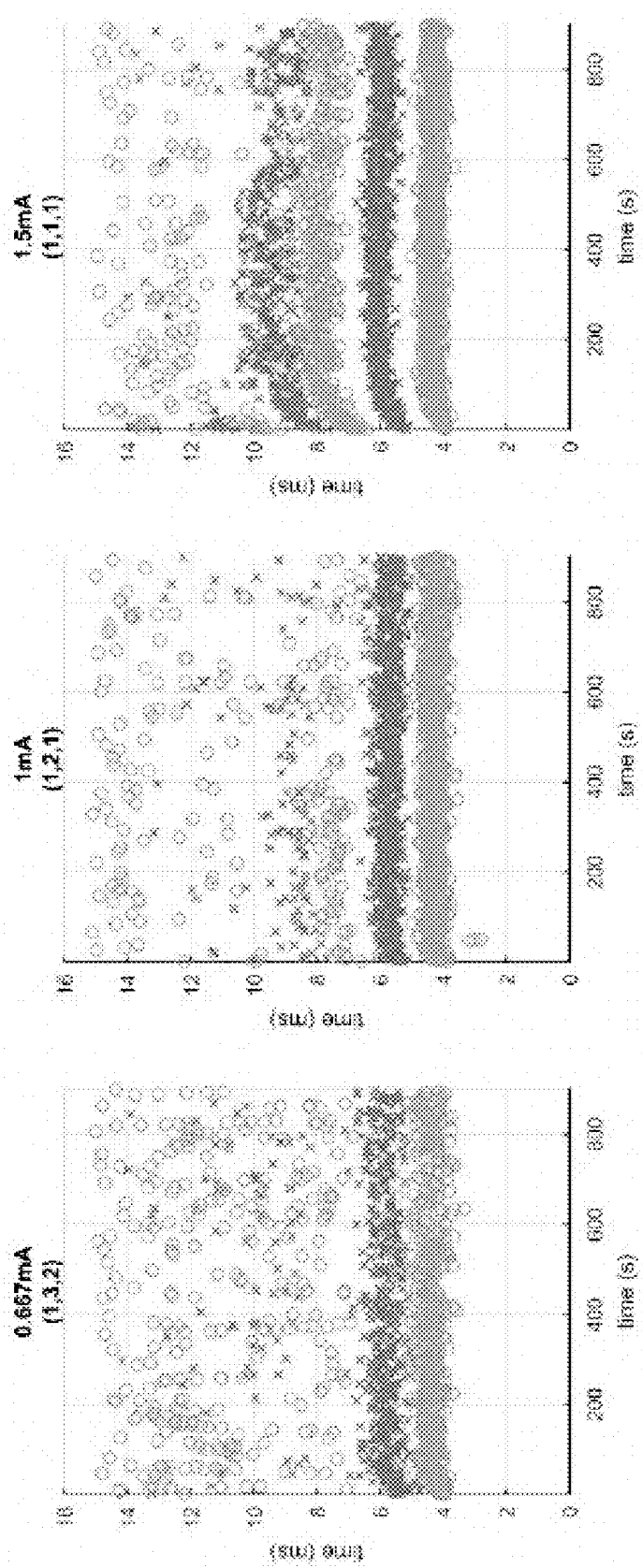
FIGS. 21A to 21G are graphical illustration showing neural resonance evoked by a continuous therapeutic patterned DBS signal.

FIGS. 21A, 21B, 21C, 21D and 21E show data extracted from ERNA waveforms recorded during patterned therapeutic stimulation with amplitudes of 0.667 mA, 1 mA, 1.5 mA, 2.25 mA and 3.375 mA respectively. In particular, this data is representative of ERNA waveforms recorded in response to the final stimulation pulse preceding a period of no stimulation (skipped pulse) as described above (with reference to FIGS. 1 and 2). Patterned stimulation was applied over several minutes (represented on the horizontal axis). ERNA waveform peaks are represented by darker points. ERNA waveform troughs are represented by lighter points. FIGS. 21F and 21G show ERNA before and after continuous DBS, during periods of burst (non-therapeutic) stimulation.

Taken together, the results shown in FIGS. 20 and 21A-21G show that there is a clear correlation between ERNA and the effectiveness of DBS on alleviating movement disorders. Accordingly, these results provide further evidence that characteristics of ERNA may be used to control DBS parameter settings to optimise therapy for individual patients.

Figure 21D:
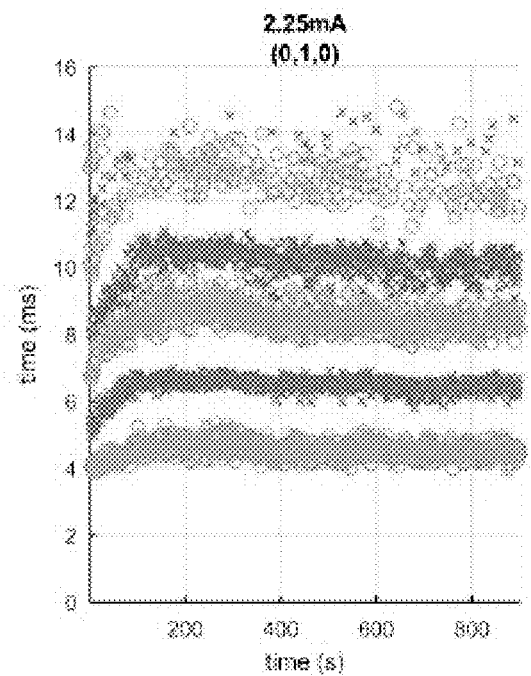
Figure 21E:
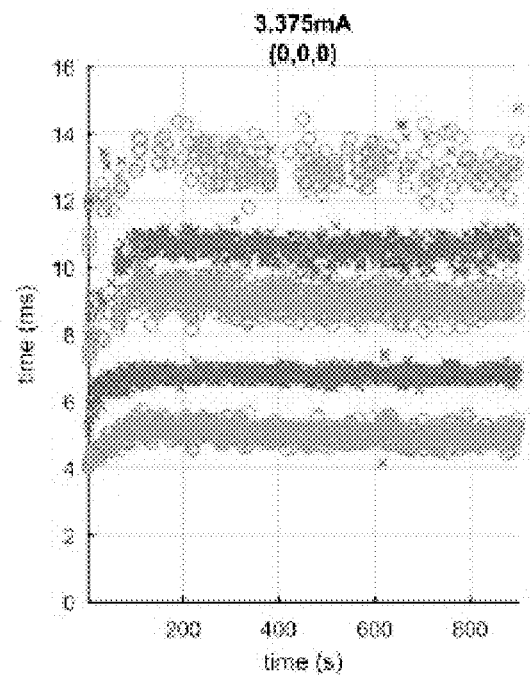
Figure 21F:
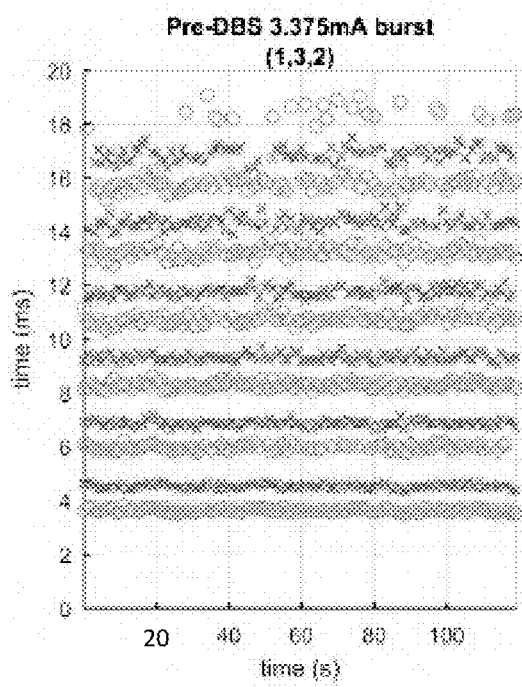
Figure 21G:
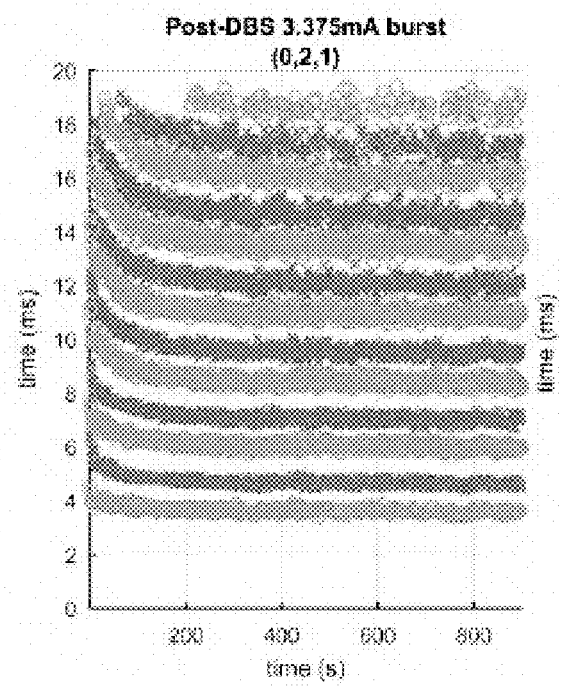
Figure 22:
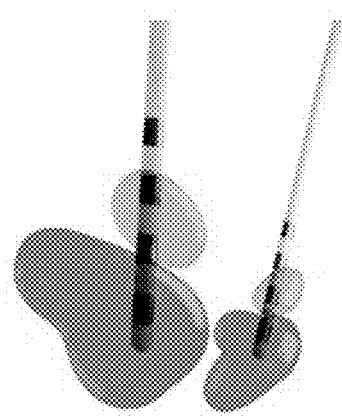
FIG. 22 is a three-dimensional reconstructions of an electrode array implanted in a STN (smaller mass) and subantia nigra. (larger mass) of a patient.

For example, if the measured ERNA waveform shows a peak at around 7 ms and an adjacent peak just below 11 ms (as shown in FIGS. 21D and 21E) then it can be assumed that DBS is effective at reducing symptoms. Peaks at these times occurred only when stimulation was applied at 2.25 mA and 3.375 mA, corresponding to DBS conditions where the patient's movement functions were less impaired (see FIG. 20). In this case, the DBS waveform can be adjusted to reduce the energy being applied to the brain. Such adjustment may comprise adjusting one or more of frequency, amplitude, pulse-width, net charge, or morphology of the stimulus. Such adjustment can minimise battery usage, reduce adverse side-effects associated with DBS, and improve safety of chronic stimulation. Otherwise, if the measured ERNA waveform shows the corresponding adjacent peaks below 7 ms and 11 ms respectively, then it can be assumed that DBS is not effective and the amplitude of DBS should be increased. For example, FIG. 21C shows adjacent peaks at approximately 6 ms and 9 ms in response to a stimulation amplitude of 1.5 mA, which was less effective at alleviating motor dysfunction as evidenced by FIG. 20.

In another example, if there are two adjacent peaks present in the ERNA waveform and they are separated in time by more than approximately 3.5 ms, as is the case in FIGS. 21D and 21E, then it can be assumed the DBS is effective. If, on the other hand, the time difference between corresponding adjacent peaks is less than 3.5 ms, as is the case in FIGS. 21A and 21B, then it can be assumed that DBS is ineffective. The DBS waveform can then be controlled to maintain DBS parameters (e.g. frequency, amplitude, pulse-width, net charge, or morphology) at levels which provides effective symptom relief whilst preferably also minimizing battery usage, reduce adverse side-effects associated with DBS, and improve safety of chronic stimulation.

Whilst the results shown in FIGS. 20 and 21A-21G show a relationship between measured ERNA and DBS amplitude in particular, it will be appreciated that a relationship exists between measured ERNA and any other parameter of the DBS waveform, including but not limited to frequency, amplitude, pulse-width, overall net charge, and morphology.

It will also be appreciated that delays in an initial peak in an ERNA waveform and delays between ERNA peaks are likely to be patient-specific. Advantageously, any reliance on such data for controlling DBS stimulation will be based on an initial characterisation of ERNA waveforms and movement impairment associated with each patient in order to generate a regime for stimulation control (e.g. closed loop control).

As has been mentioned briefly above with reference to FIGS. 20 and 21A-21G, the identification of a correlation between changes in resonant behaviour of stimulated neural circuits and a patient's disease symptoms present several opportunities to improve aspects of DBS therapy, including but not limited to techniques for initial implantation and subsequent repositioning of DBS electrodes, together with techniques for setting parameters of DBS stimulation and using feedback to adjust DBS parameters in real time whilst DBS therapy is underway.

A number of practical applications of the above described evoked resonant neural activity will now be discussed with reference to several embodiments. In the embodiments, one or more electrode leads may be used for stimulation of one or more neural structures within one or both hemispheres of the brain, each lead comprising one or more electrodes located near the tip of each lead. Each of the electrodes may be used for stimulation, monitoring, or both stimulation and monitoring. One or more of these electrodes may be implanted. Implanted electrodes may be used independently or in addition to one or more electrodes placed on the outside of the brain or skull.

Figure 8:
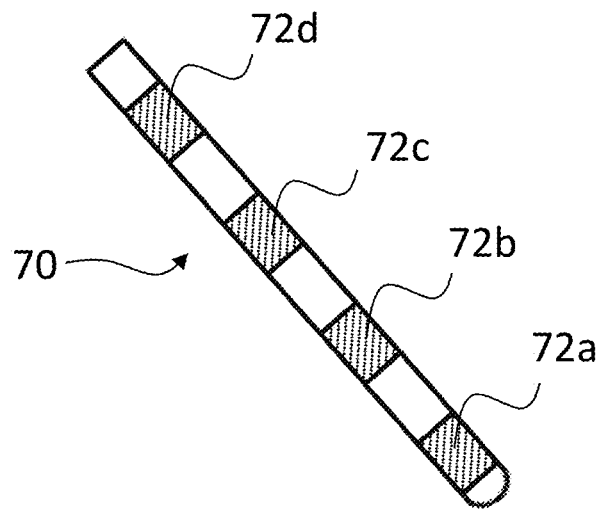
FIG. 8 is a schematic illustration of an electrode lead tip for implantation in a brain.

A typical DBS electrode lead tip 70, such as that incorporated into the Medtronic® DBS Lead Model 3387, is shown in FIG. 8. The lead tip 70 comprises a first electrode 72a, a second electrode 72b, a third electrode 72c, and a fourth electrode 72d. Once implanted into the brain, each of the electrodes 72a, 72b, 72c, 72d may be used to apply a stimulus to one or more neural structures or monitor and optionally record the evoked response (including ERNA) from neural circuits to the stimulus. In other embodiments, leads with more electrodes or electrodes with different sizes or topologies may be used. In addition, one or more reference electrodes may be located at a remote site and used to complete the electrical circuit when one or more electrodes on the DBS lead are activated for stimulation or used for signal monitoring.

The target location for the lead tip 70 varies dependent on the neural structure. Example target structures include but are not limited to the subthalamic nucleus (STN), the substantia nigra pars reticulata (SNr), and the globus pallidus interna (GPi).

Figure 9:
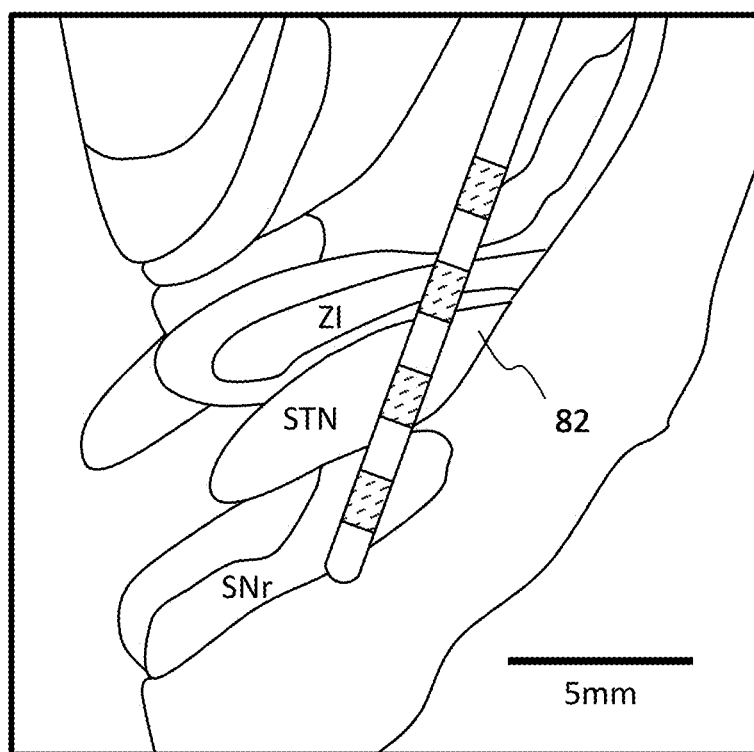
FIG. 9 is a schematic illustration of an electrode lead implanted in the subthalamic nucleus of a brain.

FIG. 9 shows the lead tip 70 implanted into a brain at a target structure, in this case the subthalamic nucleus (STN) 82. It will be appreciated that intersecting the electrode tip 70 with the subthalamic nucleus (STN) 82, which has a typical diameter of 5 to 6 mm, can be a very difficult surgical task. Techniques such as stereotactic imaging, microelectrode recordings, intraoperative x-ray imaging, and applying therapeutic stimulation whilst monitoring patient symptoms, are currently used to localise the electrode tip 70. However, these methods can lack accuracy. Additionally, existing methods usually require the patient to be awake for the procedure, since voluntary responses from the patient can be used to confirm that the electrode is at a suitable location relative to a target structure in the brain. For this reason, many potential recipients of DBS therapy turn down the option because they are not comfortable with having to be awake during the surgical procedure.

The accuracy of locating electrodes of the electrode tip 70 within a target structure can be greatly increased by using a series of patterned stimulations to generate and measure an evoked resonant response from a neural target. Such techniques can obviate the need for the patient to be awake during the implantation procedure, since an electrode can be located much more accurately at the correct location within the brain and relative to a target neural structure. This means that patients can be under sedation or general anaesthetic during the surgery since no patient feedback is required to locate the electrode to a satisfactory degree of accuracy.

Figure 10:
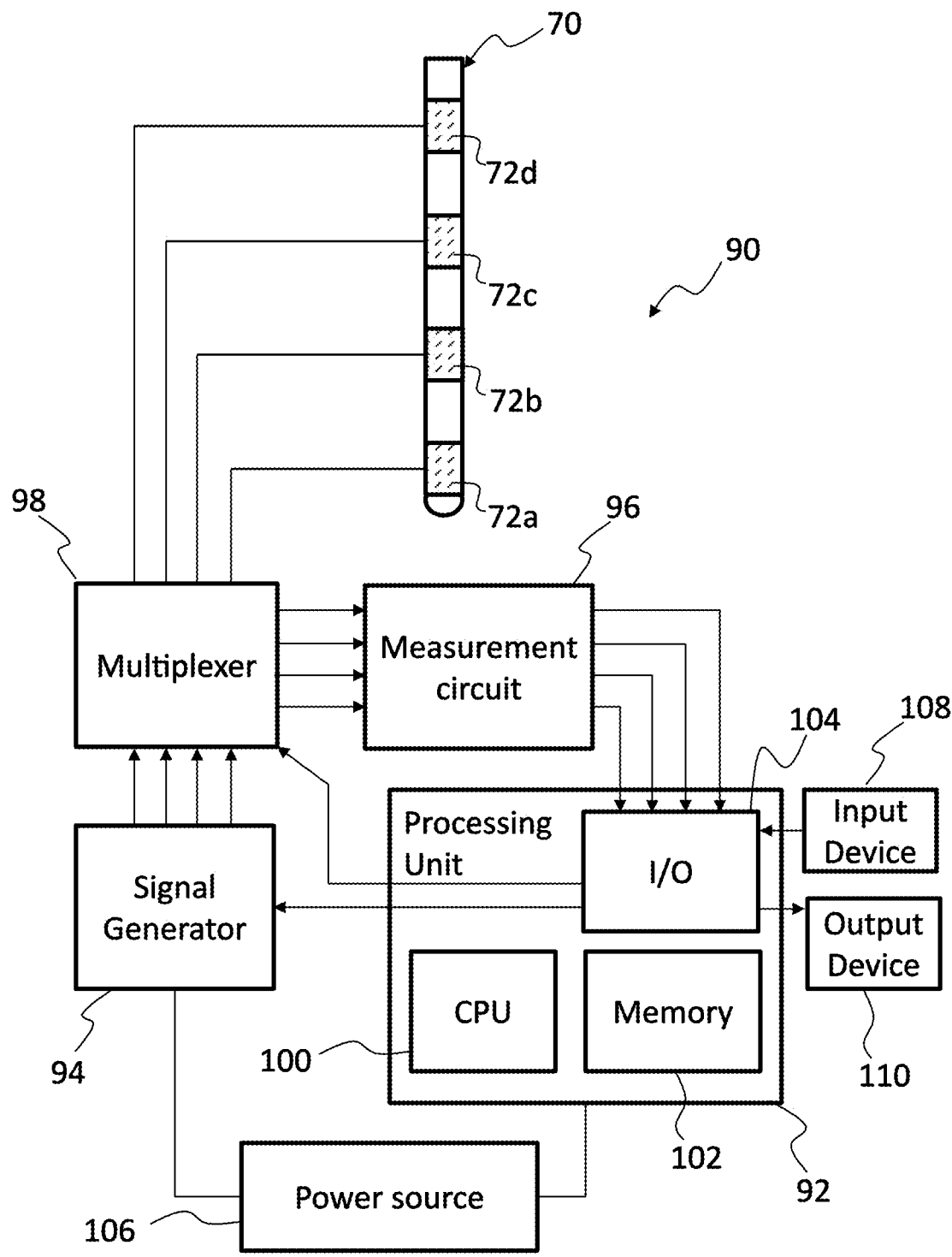
FIG. 10 is a schematic illustration of a system for administering DBS.

An example DBS delivery system 90 according to an embodiment of the present disclosure is illustrated in FIG. 10. The system 90 comprises the lead tip 70 of FIG. 8 including the plurality of integrated electrodes 72a, 72b, 72c, 72d, together with a processing unit 92, a signal generator 94, a measurement circuit 96 and an optional multiplexer 98. The processing unit comprises a central processing unit (CPU) 100, memory 102, and an input/output (I/O) bus 104 communicatively coupled with one or more of the CPU 100 and memory 102.

In some embodiments, the multiplexer 98 is provided to control whether the electrodes 72a, 72b, 72c, 72d are connected to the signal generator 94 and/or to the measurement circuit 96. In other embodiments the multiplexer may not be required. For example, the electrodes 72a, 72b, 72c, 72d may instead be connected directly to both the signal generator 94 and the measurement circuit 96. Although in FIG. 10 all of the electrodes 72a, 72b, 72c, 72d are connected to the multiplexer 98, in other embodiments, only one or some of the electrodes 72a, 72b, 72c, 72d may be connected.

The measurement circuit 96 may include one or more amplifiers and digital signal processing circuitry including but not limited to sampling circuits for measuring neural responses to stimulation, including ERNA. In some embodiments the measurement circuit 96 may also be configured to extract other information from received signals, including local field potentials. The measurement circuit 96 may also be used in conjunction with the signal generator 94 to measure electrode impedances. The measurement circuit 96 may be external to or integrated within the processing unit 92. Communication between the measurement circuit 96 and/or the signal generator 94 on the one hand and the I/O port on the other may be wired or may be via a wireless link, such as over inductive coupling, WiFi®, Bluetooth® or the like. Power may be supplied to the system 90 via at least one power source 106. The power source 106 may comprise a battery such that elements of the system 90 can maintain power when implanted into a patient.

The signal generator 94 is coupled via the multiplexer 98 to one or more of the electrodes 72a, 72b, 72c, 72d and is operable to deliver electrical stimuli to respective electrodes based on signals received from the processing unit 92. To this end, the signal generator 94, the multiplexer 98 and the processing unit 92 are also communicatively coupled such that information can be transferred therebetween. Whilst the signal generator 94, multiplexer 98, and the processing unit 92 in FIG. 10 are shown as separate units, in other embodiments the signal generator 94 and multiplexer may be integrated into the processing unit 92. Furthermore, either unit may be implanted or located outside the patient's body.

The system 90 may further comprise one or more input devices 108 and one or more output devices 110. Input devices 108 may include but are not limited to one or more of a keyboard, mouse, touchpad and touchscreen. Examples of output devices include displays, touchscreens, light indicators (LEDs), sound generators and haptic generators. Input and/or output devices 108, 110 may be configured to provide feedback (e.g. visual, auditory or haptic feedback) to a user related, for example, to characteristics of ERNA or subsequently derived indicators (such as proximity of the electrode 70 relative to neural structures in the brain. To this end, one or more of the input devices 108 may also be an output device 110, e.g. a touchscreen or haptic joystick. Input and output devices 108, 110 may also be wired or wirelessly connected to the processing unit 92. Input and output devices 108, 110 may be configured to provide the patient with control of the device (i.e. a patient controller) or to allow clinicians to program stimulation settings, and receive feedback of the effects of stimulation parameters on ERNA characteristics.

One or more elements of the system 90 may be portable. One or more elements may be implantable into the patient. In some embodiments, for example, the signal generator 94 and lead 70 may be implantable into the patient and the processing unit 92 may be external to the patient's skin and may be configured for wireless communication with the signal generator via RF transmission (e.g. induction, Bluetooth®, etc.). In other embodiments, the processing unit 92, signal generator 94 and lead 70 may all be implanted within the patient's body. In any case, the signal generator 94 and/or the processing unit 92 may be configured to wirelessly communicate with a controller (not shown) located external to the patient's body.

One embodiment of the present disclosure provides a system and method for localising the lead tip 70 within a target structure of the brain using measured ERNA. During an operation for implantation of the lead tip 70 into the brain, instead of relying on low accuracy positioning techniques as described above to estimate the location of electrodes relative to neural structures within the brain, the system 90 may be used to provide real-time feedback to the surgeon based on characteristics such as the strength and quality of evoked response signals received from one or more electrodes of the lead tip 70. This feedback may be used to estimate position within the target structure in three dimensions and to inform the decision of whether to reposition the electrodes or remove and reimplant the electrodes along a different trajectory.

Figure 11:
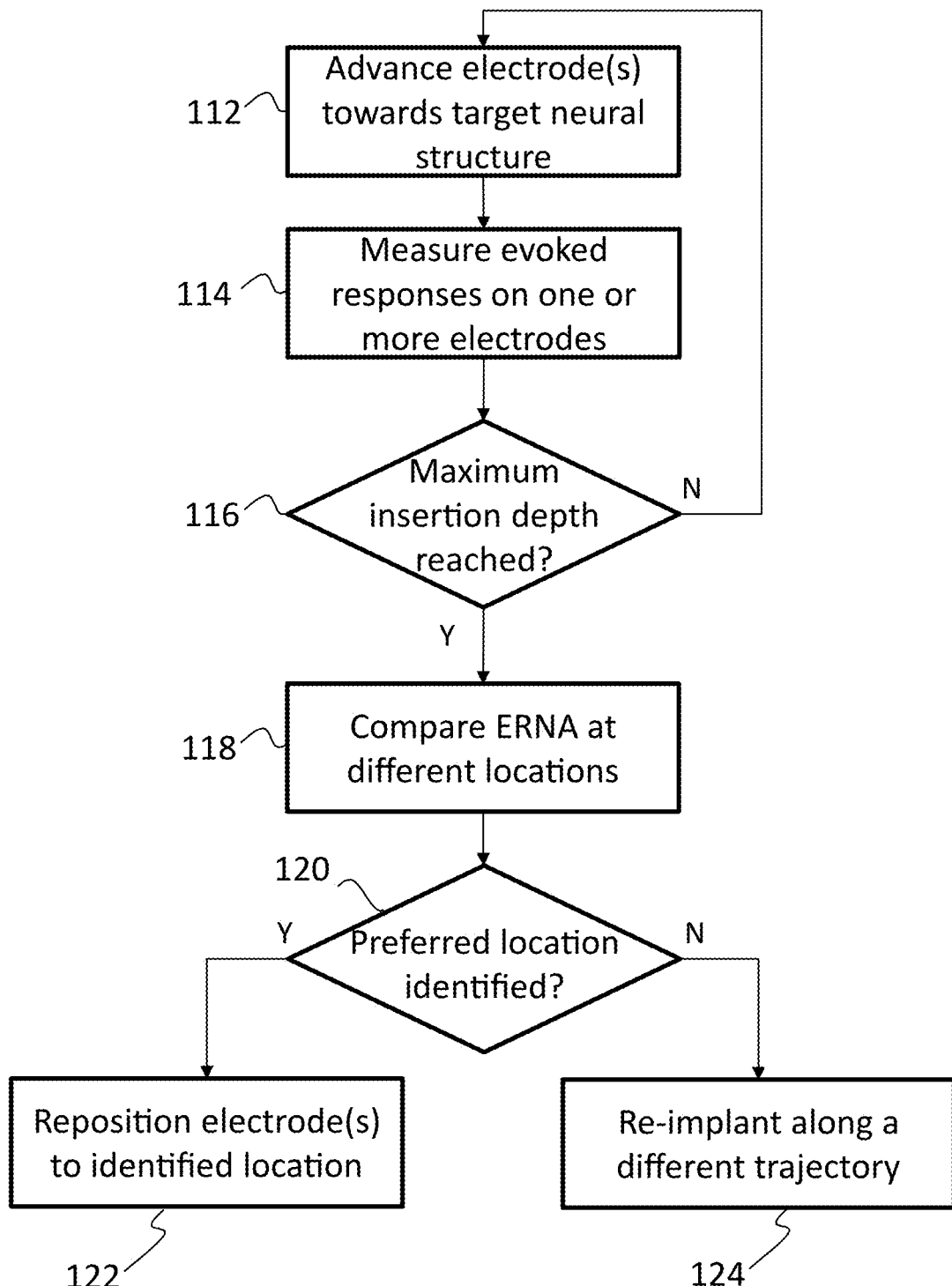
FIG. 11 is a flow diagram illustrating a process for locating a DBS electrode in the brain.

FIG. 11 shows a general example of such a process. The process begins at step 112 with an electrode lead tip such as that described with reference to FIG. 8 being advanced during surgery towards a target neural structure along a predefined trajectory. The step size (or spatial resolution) by which the electrode lead is advanced may be chosen by the surgeons and/or clinicians. In some embodiments, the step size is 1 mm. At step 114, evoked responses, including ERNA, are measured by applying a patterned stimulus such as those described above to an electrode of the lead tip 70. The stimulus may be applied for the whole time whilst the lead tip 70 is being implanted. Alternatively, the patterned signal may be repeated a predetermined number of times, such as 10 times. The evoked response may be measured at the same electrode as that used to apply the stimulus or may be measured at one or more different electrodes. By doing so, a more accurate estimate of the location of each electrode relative to the target neural structure may be provided. Steps 112 and 114 are repeated until the electrode lead tip has been inserted to the maximum allowable depth, which may be in the target neural structure or slightly beyond it.

By repeating steps 112 and 114, a profile or map of evoked responses at different locations along the insertion trajectory may be generated. The profile of evoked responses may include measurements from multiple electrodes or from just one electrode. The profile of evoked responses at different depths may be output to the one or more output devices 110. The profile of evoked responses are then compared at step 118 in order to determine whether a preferred electrode location can be identified. The identification of preferred electrode location may be based on different ERNA features, including relative differences between or spatial derivatives of amplitude, rate of decay, rate of change, and frequency, at different insertion positions (e.g. the location that produces the largest resonances).

The identification of a preferred electrode location may also be based on comparison with template ERNA activity, where the templates have been derived from recordings from other patients. The profile of evoked responses may also be used to estimate the trajectory of the electrode lead 70 through the target neural structure, including the boundaries of the structure and the region intersected (e.g. the trajectory passed through the medial or lateral region). The profile of evoked responses may also be used to estimate the proximity to the target structure, in the event that the target structure is not intersected by the insertion trajectory.

If at step 120 a preferred electrode location can be identified, the electrode lead tip 70 can be repositioned at step 122, such that an electrode is positioned at the preferred location. Alternatively, for embodiments that include electrode lead tips with a large number of electrodes, the electrode positioned closest to the preferred location can be nominated for subsequent use in applying therapeutic stimulation. If at step 120 a preferred location cannot be identified, the surgeon and/or clinician may choose to remove the electrode and re-implant along a different trajectory.

Another embodiment of the present disclosure provides a system and method for determining the relative positions of an array of electrodes with respect to a target neural structure and then selecting a preferred electrode to use for applying therapeutic stimulation. This process could be performed during electrode implantation surgery to assist in the positioning of electrodes, or with previously implanted electrodes when programming the device to deliver therapeutic stimulation. A stimulus may be applied at more than one of the electrodes of the array, for example two or more of electrodes 72a, 72b, 72c, 72d in the case of electrode array 70. Where a patterned stimulation regime is used, sequential bursts of a stimulus pattern may be applied to different ones of the electrodes 72a, 72b, 72c, 72d. Alternatively, a full stimulus pattern may be applied at one electrode, followed by another full stimulus pattern at another electrode. By doing so, a determination may be made concerning which electrode of an electrode array is positioned best to provide therapeutic stimulation to one or more of the target neural structures; for example, which of the electrodes 72a, 72b, 72c, 72d is best positioned within a target neural structure.

Figure 12:
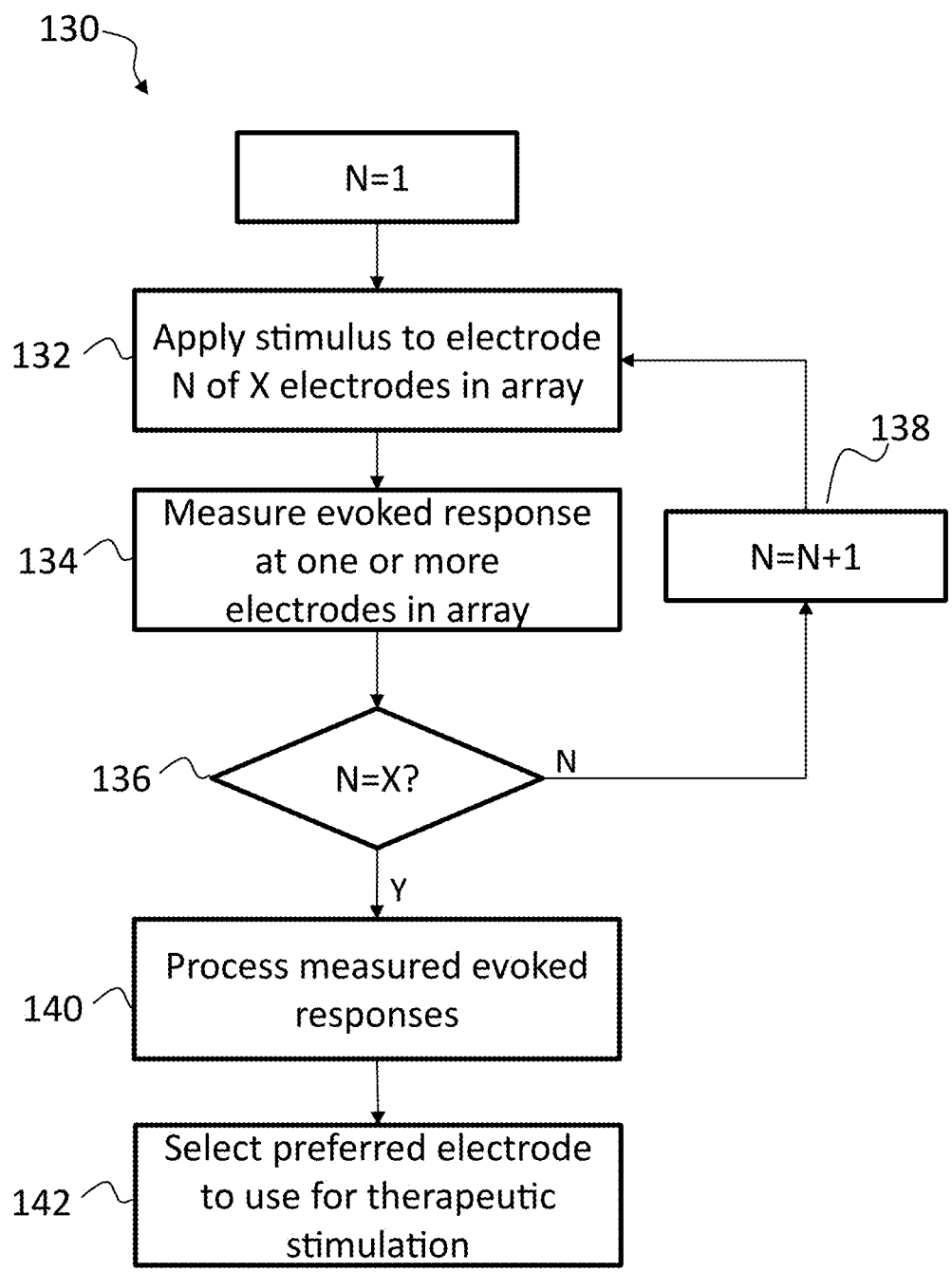
FIG. 12 is a flow diagram illustrating a process for monitoring and processing resonant responses at multiple electrodes in response to stimulation at multiple electrodes.

FIG. 12 illustrates an example process 130 for measuring evoked response from an array of multiple electrodes. At step 132, a stimulus is applied to the first electrode of an array of X electrodes (electrode 72a in the case of the lead tip 70). The stimulus applied may be a burst patterned stimulus as described above. The evoked response from a target neural structure is measured at one or more of the electrodes in the array at step 134. In the case of the lead tip 70, for example, the evoked response may be measured at the second, third and fourth electrodes 72b, 72c, 72d when the first electrode 72a is being stimulated. In some embodiments, the evoked responses received at the stimulating electrode may also be recorded and optionally stored in memory. Once the evoked response has been measured at each electrode, another electrode is selected for stimulation. This may be achieved by incrementing a counter, as shown in step 138, after the process has checked at step 136 to see whether all electrodes in the array of X electrodes have been stimulated, i.e. whether the process has cycled through all of the electrodes in the system. If there are electrodes remaining to be stimulated, then the process repeats, applying a stimulus to the next selected electrode in the array. If all electrodes in the array have been stimulated and an evoked response to stimulation at each electrode measured and recorded, the resultant measured evoked responses are then processed at step 140.

Processing the evoked responses may involve comparing different ERNA features, including relative differences between or spatial derivatives of amplitude, rate of decay, rate of change, and frequency, across different combinations of electrodes used for stimulation and measurement. For example, the processing may involve. identifying the electrode that measures the largest evoked resonance amplitude for each stimulation condition). The identification of the preferred electrode location may also be based on a comparison with template ERNA activity. Templates may be derived from recordings from other patients or from one or more models or simulations.

Based on the processing of the evoked responses, a preferred electrode to use for therapeutic stimulation may be chosen at step 142. The results of the ERNA processing and a recommendation for the preferred electrode may be output to the one or more output devices 110. If the process has been performed during surgery, the results of the ERNA processing may also be used to determine which electrodes are within the target neural structure and whether to reposition the electrode array. The results may also be used to generate one or more templates for future processing of evoked responses in the same or different patients.

Figure 13:
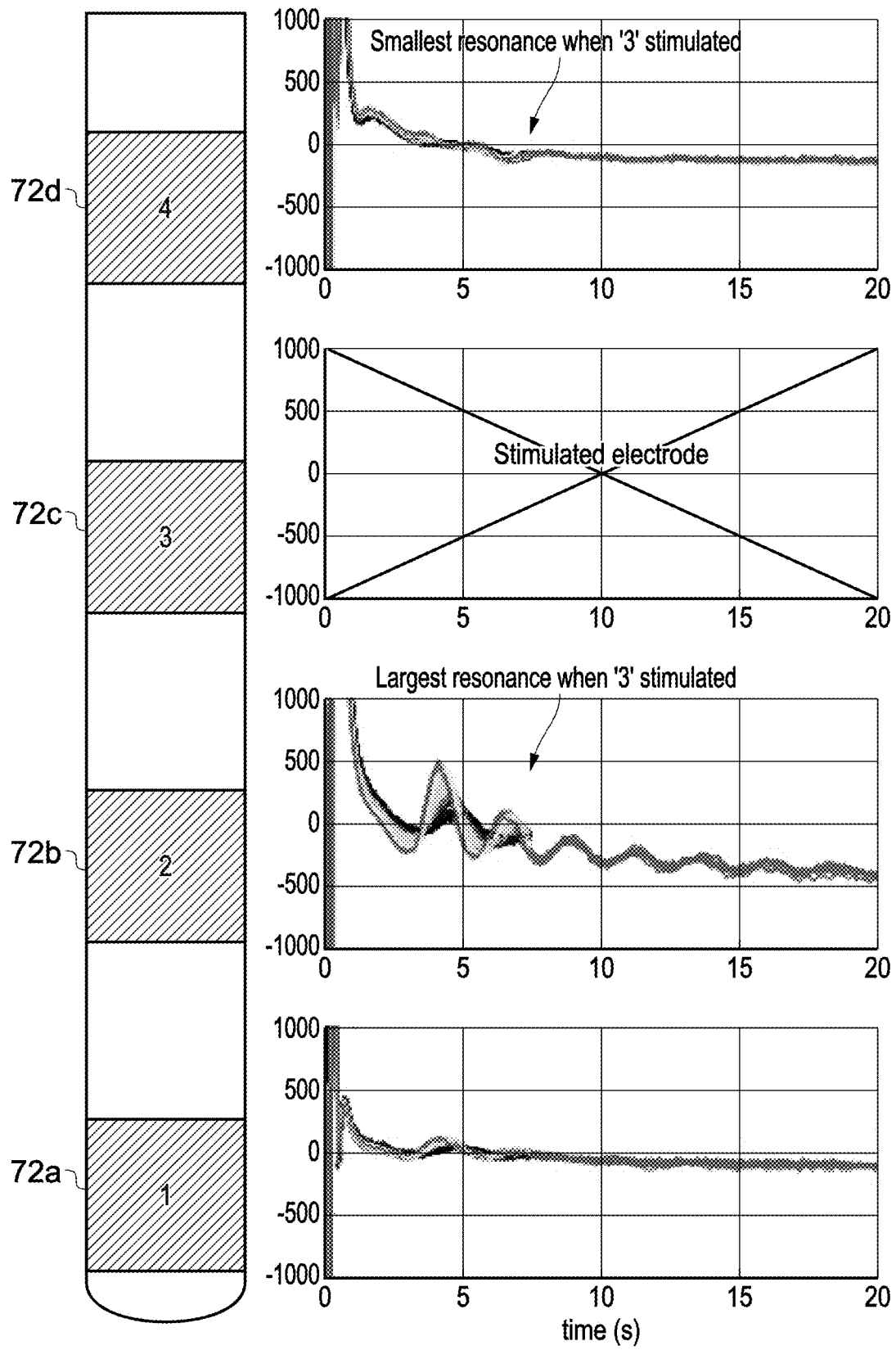
FIG. 13 is a graphical illustration of resonant responses measured at different electrodes implanted in a brain responsive to a stimulation signal in accordance with the process shown in FIG. 12.

FIG. 13 shows an example of the evoked responses measured at each of the first, second and fourth electrodes 72a, 72b, 72d based on patterned stimulation applied to the third electrode 72c. This example corresponds to one iteration of steps 132 and 134 of process 130 shown in FIG. 12. The stimulated electrode 72c is represented with the crossed axes. Firstly, it is shown that a resonant response over several cycles can be measured using the novel patterned stimulus. Secondly, it can be seen that the response at the second electrode 72b has the largest amplitude, the amplitude of response at the fourth electrode 72d has the smallest amplitude, and the amplitude of the evoked response at the first electrode 72a is substantially less than that at the second electrode 72b but slightly greater than that at the fourth electrode 72d. These results indicate that the second electrode 72b is closest to or within the target neural structure and the first and fourth electrodes 72a, 72d are outside of the target neural structure.

Whilst in the above example the evoked response is measured at three electrodes, in other embodiments, the evoked response may be measured at one or two or any number of electrodes in any configuration. For example, ERNA could be measured and/or recorded from different combinations of electrodes. Additionally or alternatively, measurement electrodes may implanted in and/or positioned external to the brain or skull.

Figure 14:
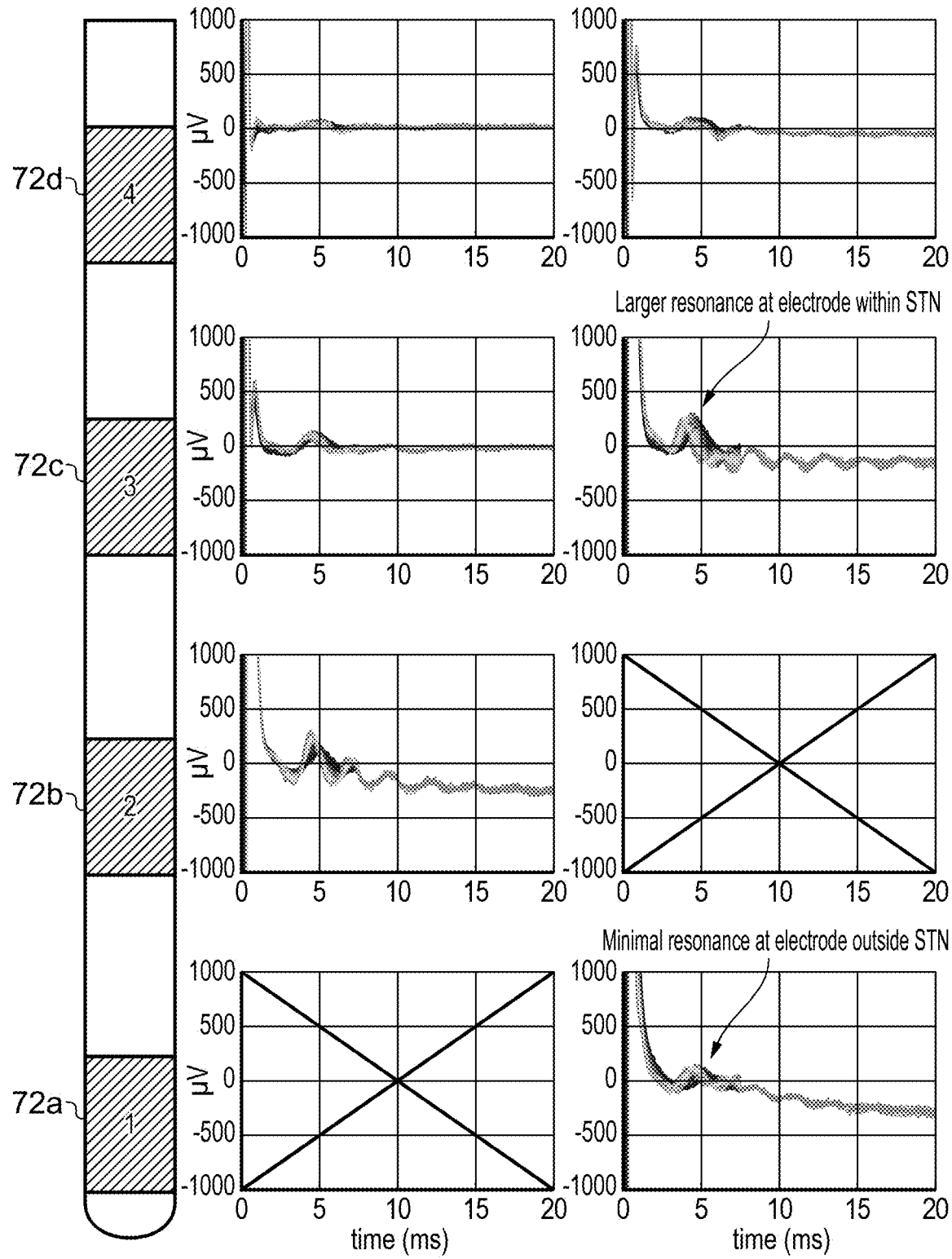
FIG. 14 is a graphical illustration of resonant responses measured at different electrodes implanted in a brain responsive to stimulation signals applied at different electrodes in accordance with the process shown in FIG. 12.
Figure 14:
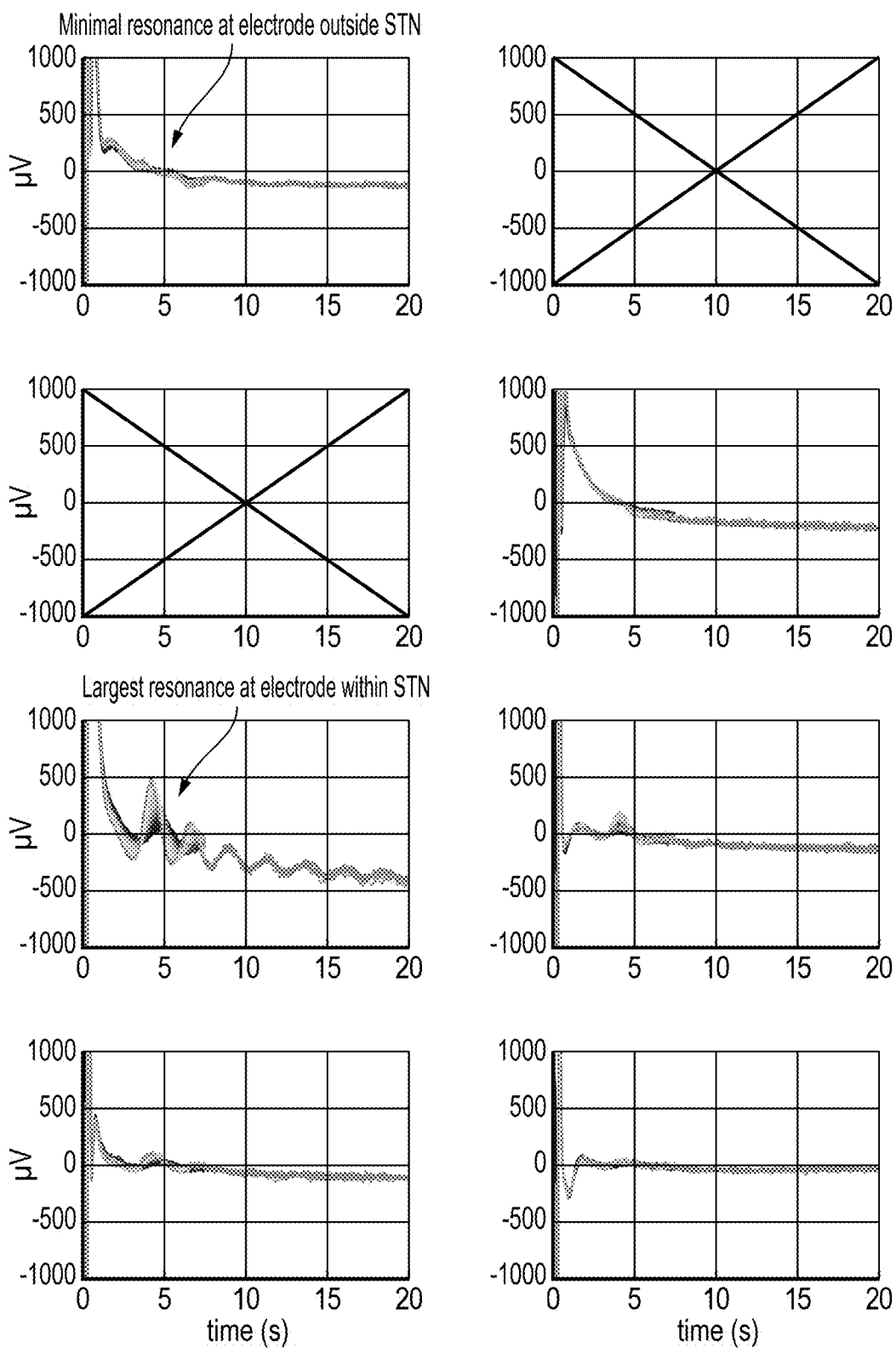

FIG. 14 graphically illustrates example evoked responses to stimulation in accordance with the process 130 of FIG. 12 applied to the lead tip 70 of the system 90 shown in FIG. 10. Each column of graphs represents one of four stimulation conditions with the stimulated electrode represented by the crossed panel, i.e. each column is an iteration of steps 132 and 134 of process 130. The data shown in FIG. 14 was measured with the second and third electrodes 72c, 72d positioned within the subthalamic nucleus (STN) of a patient's brain. It can be seen that the largest evoked responses are observed at each of the second and third electrodes 72b, 72c when the other of those electrodes 72c, 72b is stimulated. Accordingly, by comparing the measured evoked responses at each electrode in response to stimulation at another electrode, a determination can be made firstly of whether any of the electrodes are positioned within the target neural structure, secondly whether any of the electrodes are positioned at an optimum location within the target neural structure, and thirdly the direction and/or distance of a particular electrode from that target neural structure. In some embodiments, one or more of the presence, amplitude, natural frequency, damping, rate of change, envelope, and fine structure of a evoked resonant response to a stimulus may be used to identify the most effective electrode in an electrode array. Additionally, it can be seen that the evoked responses vary depending on the position of the electrode used for stimulation, illustrating the feasibility of using the process illustrated in FIG. 11 to localise electrodes within a target neural structure.

The process 130 of FIG. 12 may be repeated using different stimulation parameters (e.g. using different stimulation amplitudes or frequencies) or with more than one stimulating electrode in step 132 (e.g. stimulation applied concurrently through multiple electrodes on one or more electrode leads). The response characteristics obtained may be used to aid current steering (e.g. setting the distribution of currents across electrodes that are active simultaneously) and the selection of active electrodes (e.g. which electrodes to use for stimulation). For example, response characteristics can be used to estimate the spatial spread of activation relative to the target area. Using this information, the stimulation profile may be shaped using two or more electrodes to direct stimulation to particular areas of the brain, i.e. towards a target structure, and away from areas which the clinician does not wish to stimulate.

In a further embodiment, ERNA can also be used to optimize stimulation parameters used to target various medical conditions. For instance, once an electrode array such as the lead tip 70 has been accurately located within a target neural structure, the setting of stimulation parameters for therapeutic DBS can be aided by measuring ERNA, improving accuracy and time- and cost-efficiency, and reducing undesirable side-effects.

The change in elicited resonant activity for different stimulation parameters may be used to optimize stimulation settings. Such processes can enable therapy to be tailored to the individual needs of patients and can be performed with minimal clinical intervention. In some embodiments, one or more of the presence, amplitude, natural frequency, damping, rate of change, envelope, and fine structure of an evoked resonant response to a stimulus may be used to optimise stimulation. Such response characteristics may be used to adjust amplitude, frequency, pulse width, and shape of a stimulation waveform.

A parameter of therapeutic stimulation that is particularly difficult to set using state of the art techniques is stimulation frequency. This is partly because optimum stimulation frequency can vary from patient to patient; typically between around 90 Hz to around 185 Hz. In embodiments of the present disclosure, one or more of the above described characteristics of ERNA may be used to set frequency of stimulation (e.g. the time period $t_2$ between pulses in a burst). For example, the stimulation frequency might be selected to approximate a multiple or submultiple of a frequency component of the ERNA, such as the estimated fundamental frequency of the ERNA.

It will be appreciated that some or all of the parameters listed above may have synergistic or adverse effects on one another and thus the effectiveness of treatment. Accordingly, in some embodiments, known optimisation techniques such as machine learning or particle swarm may be implemented to find an optimal set of parameter values within the multidimensional parameter space. Such techniques may involve an iterative process of trying a selection of different parameter settings to determine the most effective parameter values based on the monitored ERNA.

Figure 15:
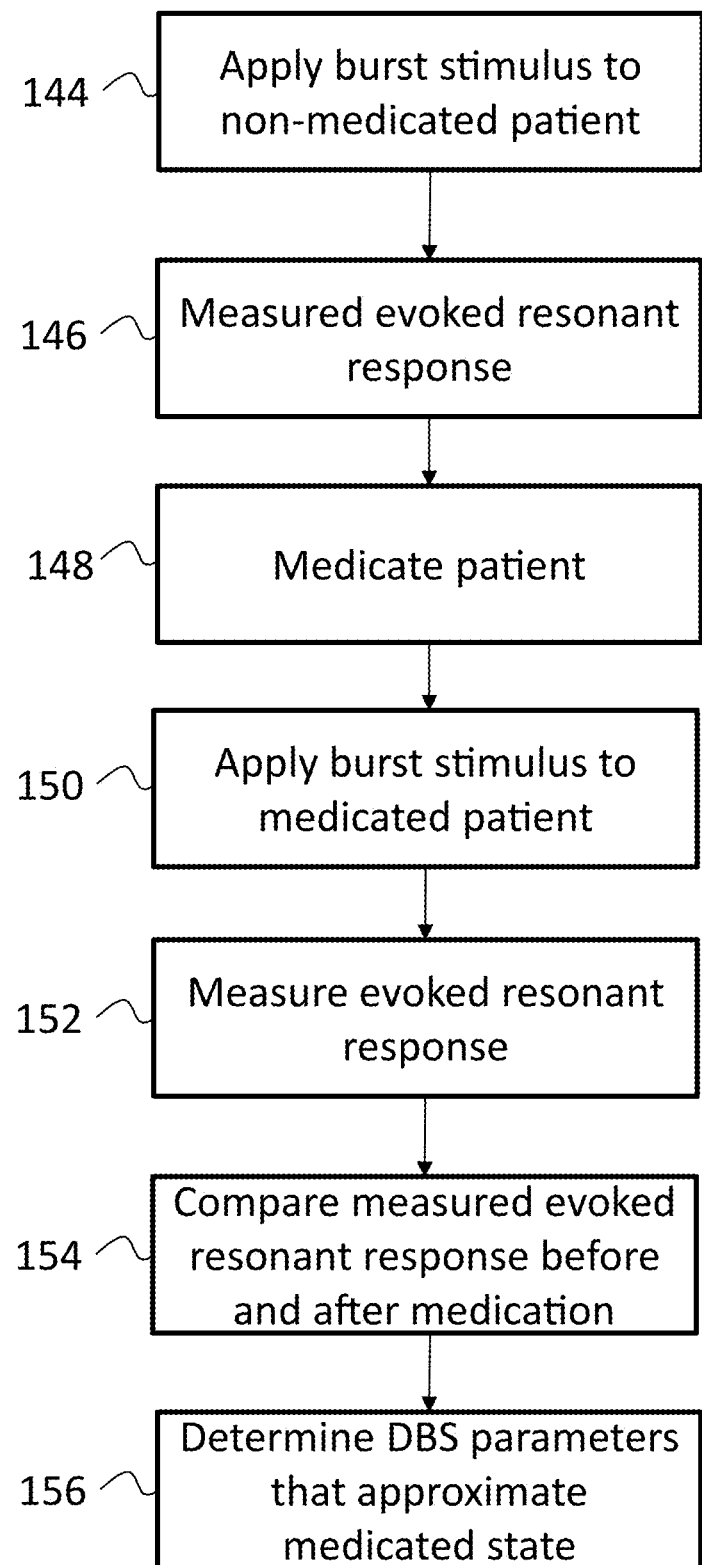
FIG. 15 is a flow diagram illustrating a process for determining parameters for a DBS stimulation signal based on medicating the patient.

To further optimise therapeutic DBS, the above techniques for ERNA monitoring and DBS parameter optimisation can be performed on a patient before and after administration of medication for relieving symptoms of a condition. For example, a record of ERNA for a particular patient who is on or off such medication may be used as a benchmark for an evoked resonant response which provides the most benefit to a patient so that parameters can be tuned to try to replicate such evoked response states. FIG. 15 schematically illustrates a method of determining stimulation parameters based on the ERNA responsive to the stimulation of a medicated patient. At step 144, a stimulus is applied to an implanted electrode in a target neural structure of a patient before being administered with any medication, and the ERNA from the stimulus is measured and recorded at step 146. The patient is then medicated at step 148. For example, a clinician may administer a dose of a drug (e.g., levodopa) to the patient. At steps 150 and 152 the process of stimulation and measurement of resonant response are repeated. The ERNA before and after the medicament is administered is then used to determine stimulation parameters which approximate those of the patient's medicated state. In particular, DBS parameter settings may be chosen which, when administered, replicate or approximate the transition from the uncontrolled-symptom ERNA to the controlled-symptom ERNA.

In some embodiments, optimisation processes may be performed by a clinician when the system 90 is being installed or during a visit to a healthcare centre. Additionally or alternatively, the optimisation may be run by the patient or may be instigated by the system 90 automatically. For example, the system 90 may implement an optimisation process periodically (e.g. every day, week or month). In other embodiments, an optimisation process could be initiated on replacement or recharge of a battery, in circumstances where the power source 106 includes a battery. Other conditions that could trigger an optimisation process include a change in the patient's state, such as whether the patient is engaged in a fine motor task, a gross motor task, speaking, sleeping, or is sedentary.

In some embodiments, the system 90 may store a series of previously optimised settings in the memory 102. These stored settings may correspond to the optimised settings for different patient states (e.g. fine or gross motor activation, sleeping or sedentary) and may include stimulation being applied to different target neural structures. The patient may be given the ability to choose which of the stored stimulation settings they want to use at any given time, through the use of a patient controller. Alternatively, the system 90 may automatically choose which of the stored stimulation settings to use based on measurements of the patients state from electrophysiological signals (e.g. ERNA or local field potentials) recorded from the electrodes 70 by system 90 or from measurements taken with input devices 108 of system 90 (e.g. accelerometers).

In addition to enhancing the accuracy of locating a DBS electrode in the brain, choosing electrode configurations for stimulation and optimising stimulation parameters, ERNA may be used to generate feedback for controlling the stimulation of electrodes. In some embodiments, feedback may be implemented using the system 90 shown in FIG. 10.

In one embodiment, the system 90 may use a waveform template corresponding to a preferred patient state. The template may be generated using previous recordings of ERNA in a patient with reduced symptoms. For example, ERNA templates recorded from a medicated patient or a patient receiving effective stimulation treatment may be used. Alternatively, ERNA templates recorded from a healthy patient, e.g. a patient without a movement disorder, may be used. Templates may be constructed from the average of many recordings from one patient or several patients. In some embodiments, selected features of the ERNA waveform may be used instead of a complete template. For example, parameters of the ERNA such as the dominant frequency and amplitude components and/or temporal features may be used to enable improved electrode placement and control of therapeutic stimulation. In some embodiments, preferred ranges for different ERNA characteristics may be defined (e.g. stimulation is controlled such that the ERNA frequency remains within 250-270 Hz).

Figure 16:
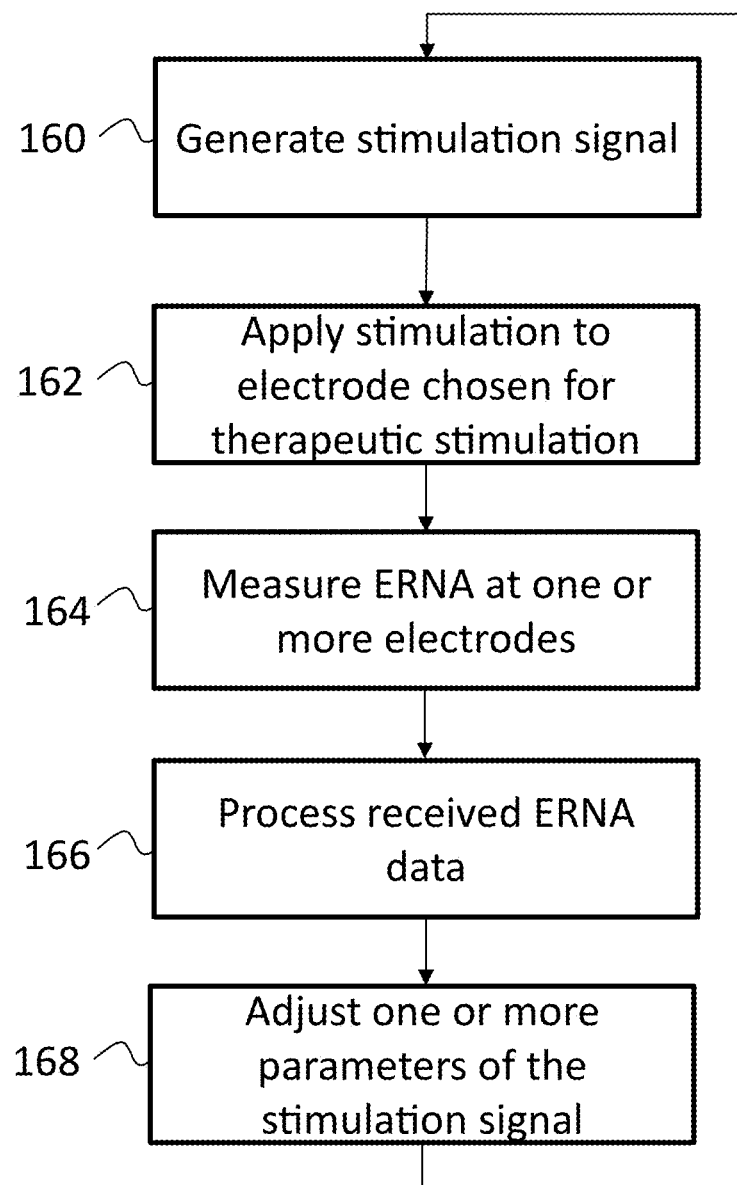
FIG. 16 is a flow diagram illustrating a process for generating a stimulation signal with closed-loop feedback based on evoked resonance at a target neural structure.

Referring to FIG. 10 and FIG. 16, the processing unit 92 may send instructions/signals to the signal generator 94 to generate a patterned stimulation signal which may or may not have been pre-calibrated in accordance with an embodiment described above. The signal generator 94 may then generate the signal at step 160 and apply it to one of the electrodes 72a, 72b, 72c, 72d of the lead tip 70 (step 162). The processing unit 92 may then measure the ERNA and monitor one or more parameters (or characteristics) of the ERNA (step 164). The processing unit 92 may then process the received ERNA data (step 166). In some embodiments, the processing unit 92 may compare the ERNA (or one more parameters thereof) with a resonant response associated with effective therapy (or one or more parameters thereof). Based on the ERNA data, the processing unit 92 may then instruct the signal generator to adjust one or more parameters of the stimulation signal applied to one of the electrodes 72a, 72b, 72c, 72d (step 168).

In some embodiments, bursts of stimulation, such as those described above, in combination with the monitoring of ERNA may be used to identify a therapeutic resonant state (e.g. a state which correlates with good symptom suppression with minimal side effects and/or minimum electrical power consumption). From this information, therapeutic stimulation parameters required to produce the preferred therapeutic state may be identified. In some embodiments, these stimulation parameters may be used to apply continuous therapeutic DBS to the target neural structure.

Probe bursts for identifying resonant activity can be interleaved with the therapeutic DBS to re-assess the resonant state. These probe bursts may be implemented on a periodic basis, for example, every 10 seconds. In one embodiment, every 10 seconds, a probe burst may be applied for 1 second (e.g. 10 pulses at 130 Hz) and the ERNA assessed. The therapeutic stimulation parameters may then be adjusted or maintained based on the ERNA. For example, if there is a change in ERNA relative to the last probe burst, the stimulation parameters may be adjusted such that the ERNA becomes comparable with the previously measured ERNA and/or the template ERNA and/or an ERNA characteristic is within a desired range.

There are a number of ways in which the therapeutic stimulation may be adjusted based on the measured ERNA. In some embodiments, if the resonant circuit is in a preferred resonant state, e.g. if the measured ERNA substantially matches a template or if an ERNA characteristic is within a desired range, the amplitude of the therapeutic stimulation may be reduced by the signal generator 94 in response to an instruction from the processing unit 92. Conversely, if the neural circuit is not in a preferred resonant state, the amplitude of therapeutic stimulation may be increased by the signal generator 94.

In some embodiments, if a therapeutic resonance is detected, the DBS stimulation may be switched off altogether or until after the next probe burst is applied to generate a measurable ERNA. Then when the next probe burst is applied, if the resonance is no longer therapeutic, the DBS stimulation may be switched back on.

In some embodiments, a comparison of multiple resonant components in a single measured evoked response may be used as a measure of stimulation efficacy and may be used as a control variable to control stimulation parameters.

In some embodiments, the length of continuous stimulation blocks (between probe bursts) and the duration of the probe bursts may be adjusted to optimise the ERNA. Longer continuous stimulation periods or blocks between probe bursts will reduce the computation load on the processing unit 92 and thus increase power efficiency but may also result in greater variation of ERNA from the preferred ERNA and thus a reduction in effectiveness of treatment.

Figure 17:
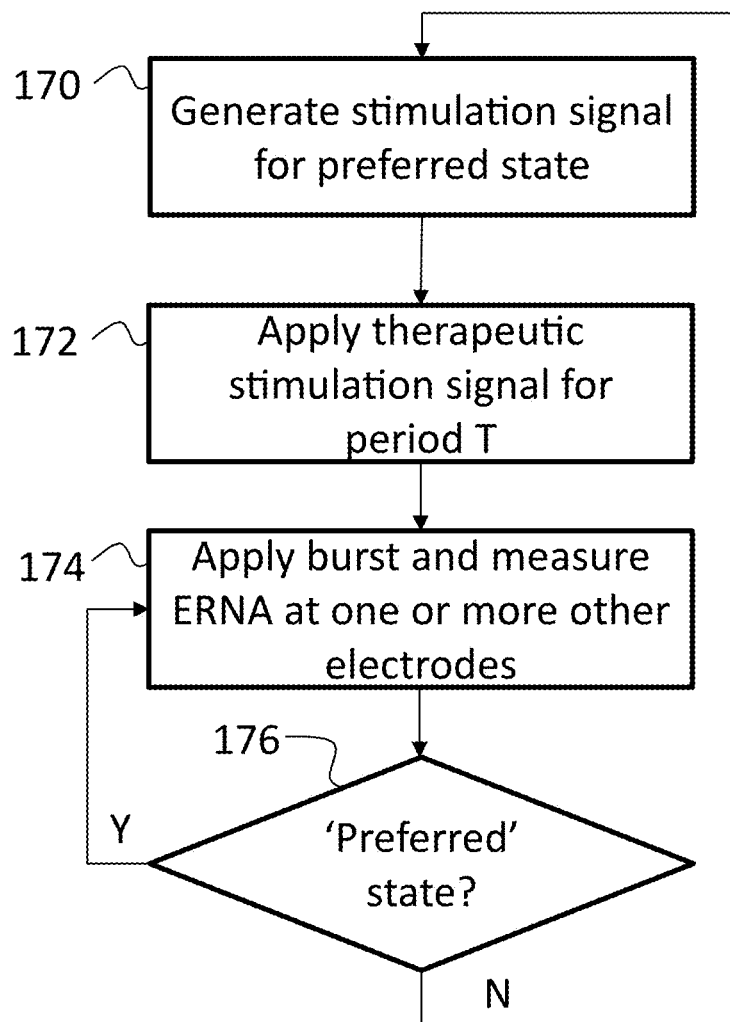
FIG. 17 is a flow diagram illustrating another process for generating a stimulation signal with closed-loop feedback based on evoked resonance at a target neural structure.

There is an inherent requirement for implanted and portable DBS devices to provide the best treatment of symptoms while minimising both side effects and power consumption. In one embodiment, a method for operating the system 90 using closed-loop feedback is provided in which the duty cycle of stimulation is modulated with an aim to minimise stimulation on-time. FIG. 17 illustrates a process which may be performed by the system 90. At step 170 a stimulation signal is generated. Parameters of the stimulation signal are chosen so as to optimise the ERNA to a preferred resonant state. The stimulus is then applied to an electrode of the lead tip 70 for a period T at step 172. The period T may be a fixed period. Preferably the stimulus is applied continuously or periodically until a preferred state of ERNA is reached. The therapeutic stimulation is then stopped and the evoked response is measured at one or more electrodes, the evoked response being to a probe stimulus comprising one or more bursts of pulses applied to the stimulation electrode (at step 174). In some embodiments the probe stimulus may be applied to more than one electrode. In some embodiments, the stimulation electrode can be used to measure ERNA instead of or in addition to the one or more other electrodes. The system is then maintained in this state of monitoring until the ERNA becomes undesirable. In some embodiments, the determination of whether or not the ERNA is in a preferred or therapeutic state may be performed by comparing the measured response with a template ERNA response or by comparing a measured ERNA characteristic with a desired range. As soon as it is considered that the state is undesirable at step 176, a stimulation signal is again generated and applied at steps 170 and 172.

Figure 18:
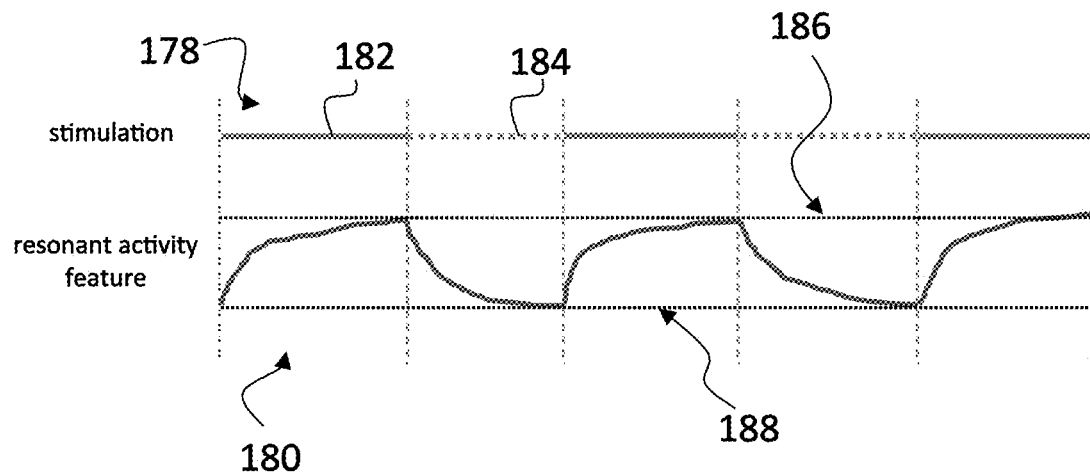
FIG. 18 graphically illustrates switching between periods of therapeutic and non-therapeutic stimulation relative to a resonant activity feature of an evoked response in accordance with the process of FIG. 17.

FIG. 18 graphically compares a stimulation regime 178 comprising a patterned therapeutic stimulation signal 182 followed by a non-therapeutic patterned stimulation signal (comprising one or more bursts of pulses) 184 and a corresponding characteristic (e.g. resonant frequency) 180 of the ERNA varying between a preferred state 186 and a less than preferable state 188.

Figure 19A:
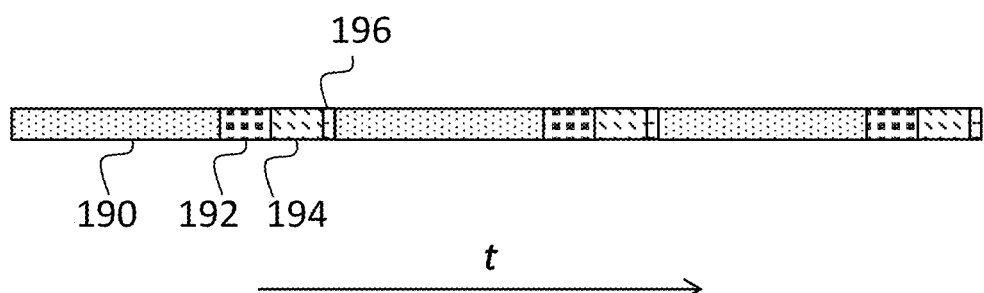
FIG. 19A illustrates a patterned stimulation signal according to an embodiment of the present disclosure.
Figure 19B:
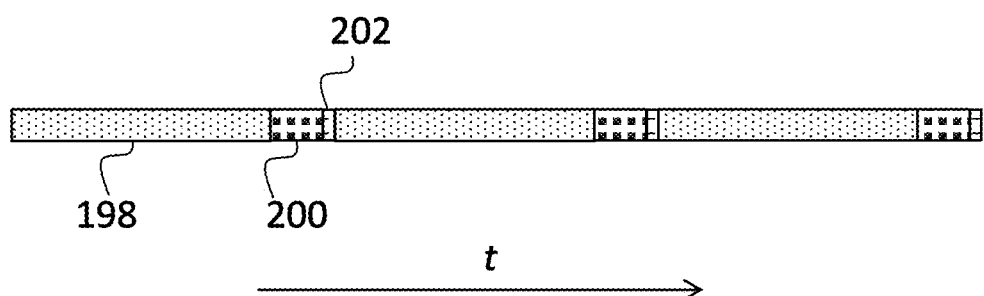
FIG. 19B illustrates another patterned stimulation signal according to an embodiment of the present disclosure

There are several different ways of implementing the patterned signals of embodiments described herein. FIGS. 19A and 19B illustrate two exemplary patterning profiles. In FIG. 19A, the patterned profile includes a period of no stimulation 192 after a continuous stimulation block 190, followed by a burst of pulses 194 and another period of no stimulation 196. During the period of no stimulation, the ERNA may be measured and therapeutic stimulation signal adjusted (if required).

In an alternative embodiment, the system may monitor the ERNA after a final pulse of continuous stimulation 198 as shown in FIG. 19B. After a period of monitoring 200, the therapeutic stimulation may then be adjusted for a period 202 after which the therapeutic stimulation 198 may be applied with the adjusted parameters. This regime may also be considered as continuous stimulation with periodic missing pulses. To this end, the continuous stimulation may be considered as a burst of pulses, and the period of no stimulation may be considered as the first time period $t_1$ as described with reference to FIG. 2 above.

In other embodiments, instead of omitting stimulation during the monitoring period 200, stimulation may be maintained but with altered parameters, as described previously with reference to FIGS. 5A and 5B. For example, conventional therapeutic stimulation at a frequency of, e.g. 130 Hz, may be applied during the therapeutic stimulation period 198. Then during the monitoring period 200, a stimulus having a different frequency, may be applied. The stimulus applied during the monitoring period may be lower than that applied during the stimulation period. For example, the stimulation frequency during this period may be in the region of 90 Hz. The frequency of this stimulus during the monitoring period 200 may be low enough to allow for multiple ERNA peaks to be observed. Equally, the frequency of the stimulus applied during the monitoring period 200 may be high enough to be within the therapeutic frequency range for DBS. As mentioned above, the transition between frequency may be abrupt or, alternatively the change in frequency may be gradual. Applying ramps to the frequency of the pulses to avoid an abrupt step change in frequency may be advantageous.

Additionally or alternatively, the amplitude of the stimulus applied during the monitoring period 200 may differ to that applied during the therapeutic period 198. For example, the amplitude of the stimulus applied during the monitoring period 200 may be less than that applied during therapeutic stimulation 198. An amplitude ramp may be applied to transition the stimulus between the therapeutic period 198 and the monitoring period 200 over several pulses, to avoid an abrupt step change in amplitude.

In some embodiments, characteristics of the stimulus other than amplitude and frequency may differ between the stimulation period 198 and the monitoring period. Examples of such characteristics include, but are not limited to, frequency, amplitude, pulse-width, net charge, electrode configuration, or morphology of the stimulus.

The presence and amplitude of ERNA can be dependent on stimulation amplitude. Accordingly, so as to maintain consistency in ERNA measurements, it may be preferable to always use the same pulse parameter settings and in particular the same amplitude for the pulse used to measure ERNA. The last pulse before the period of no stimulation may therefore be at a fixed amplitude which is independent of the amplitude of stimulation being applied by other pulses (e.g. therapeutic stimulation), so as to minimise any effect due to resonance dependence on stimulation amplitude or other pulse parameters.

Whilst in embodiments described above, a single electrode array is used both to stimulate and record an evoked neural response, in other embodiments, electrodes may be distributed on multiple probes or leads in one or more target structures in either or both brain hemispheres. Equally, electrodes either implanted or positioned external to the brain may be used to stimulate or record or both stimulate and record an evoked neural response. In some embodiments, a combination of both microelectrode and macroelectrodes may be used in any foreseeable manner.

In a further application of the embodiments of the present invention ERNA measurements may be recorded and tracked over time to monitor the progression or remission of a disease or syndrome, or used as a diagnostic tool (e.g. to classify the patient's neurological condition). Such embodiments may also be used to provide medical alerts to the patient, a caregiver or a clinician in the event that the patient's state (as determined by ERNA) deteriorates towards an undesirable or critical state (e.g. a Parkinsonian crisis).

In yet another application, ERNA may be used to monitor the effects of medication over time, including the effects of adjusting medication doses, etc. Such an embodiment may also be used to provide medication alerts to the patient to remind them when a dose is required or when a dose has been skipped. Tracking medication effects with ERNA may also provide clinicians with information regarding whether medication is being taken as prescribed or whether medication is becoming less effective and requires dosing adjustment.

Further Analysis of ERNA and Explanation of Results
DBS Evokes Resonant Neural Activity The neural activity resulting from DBS pulses was investigated to determine if there were evoked responses that could feasibly be used as a biomarker. To preserve evoked activity we used a wide recording bandwidth, as well as symmetric biphasic pulses for stimulation, rather than conventional asymmetric pulses with a very long second phase, to minimize the temporal duration of stimulation artefacts.

Recordings were made from DBS electrodes immediately following their implantation in the STN of patients with PD who were still awake on the operating table, as PD is the predominant application for DBS. Furthermore, the STN's roles in regulation of motor, limbic, and associative function make it a neural target relevant to a number of different applications, including DBS treatment of dystonia, essential tremor, epilepsy, and obsessive-compulsive disorder.

It was found that STN-DBS evokes a large peak typically around 4 ms after each pulse. By examining the activity following the last pulse prior to cessation of DBS it was discovered that this peak is the first in a series with progressively decreasing amplitude. As this response has a form that resembles a decaying oscillation, we describe it as evoked resonant neural activity (ERNA).

To further investigate ERNA, we temporally patterned standard 130 Hz DBS to allow multiple peaks to be observed. We employed two novel patterns: skipping one pulse every second, and applying a burst of ten pulses every second. The 'skipped-pulse' pattern was anticipated to have comparable therapeutic effects to standard 130 Hz DBS, as it causes only a 0.77% reduction in the total number of pulses delivered over time. In contrast, the 'burst' pattern was anticipated to have minimal therapeutic effects relative to continuous DBS, as only 7.7% of the pulses are delivered, making it a useful probe for investigating activity in the absence of therapy. The evoked responses tend to increase in amplitude and sharpen across the consecutive pulses of a burst, and reach a steady state for longer duration stimuli.

We applied the burst stimulus to the STN of 12 PD patients (n=23 hemispheres) undergoing DBS implantation surgery and observed ERNA of similar morphology in all cases, indicating it is a robust and reliable signal that can be measured across the patient population. As a control to ensure that ERNA was not a specious artefact, we also applied the burst stimulus to 3 Essential Tremor patients (n=6 hemispheres) with electrodes implanted in the posterior subthalamic area (PSA), a white matter region medial to the STN. ERNA was not observed in the PSA, suggesting it is an electrophysiological response localizable to the STN.
ERNA is Localizable to the STN To establish that ERNA varies with electrode position relative to the STN, we consecutively applied 10 s of burst stimulation to each of the four DBS electrodes whilst recording from the three unstimulated electrodes. The DBS implantation surgery aimed to position two of the four electrodes within the STN, with one electrode in the dorsal STN where DBS usually has greatest benefit and another in the ventral STN. This variance in electrode location facilitated comparison of ERNA responses from different regions of the STN with those outside of the nuclei. In 8 STN-PD patients (n=16 hemispheres), we found that both ERNA amplitude and morphology varied depending on the stimulating and recording electrode positions. FIG. 14 shows exemplar ERNA from the last pulse of each burst in one hemisphere, with the responses with the largest amplitude and most apparent decaying oscillation morphology occurring at the two middle electrodes in the target STN position. As a control, we also applied stimulation to two Essential Tremor patients (n=4 hemispheres) using an implantation trajectory intended to position distal electrodes within the PSA and proximal electrodes in the ventral intermediate nucleus of the thalamus, another target for tremor that has previously been shown not to elicit evoked activity beyond 2 ms.

Figures 23A, 23B, 23C:
FIGS. 23A to 23C are merged MRI and CT scans of a patient's brain showing the positioning of an electrode array.

As variation in ERNA amplitude was the most apparent feature, we used it for further analysis. As not all recordings were in STN and contained distinct resonant activity, to quantify ERNA amplitude we calculated the root mean square (RMS) voltage over 4-20 ms. To estimate implanted electrode positions relative to the STN, 3D reconstructions (FIG. 22) were generated using post-operative CT scans merged with pre-operative MRI (FIGS. 23A-23C). Electrodes were classified as being either superior to, inferior to, or within the STN, based on blinded measurements relative to the red nucleus. Within-STN electrodes were then further classified to be either dorsal or ventral.

Figure 24:
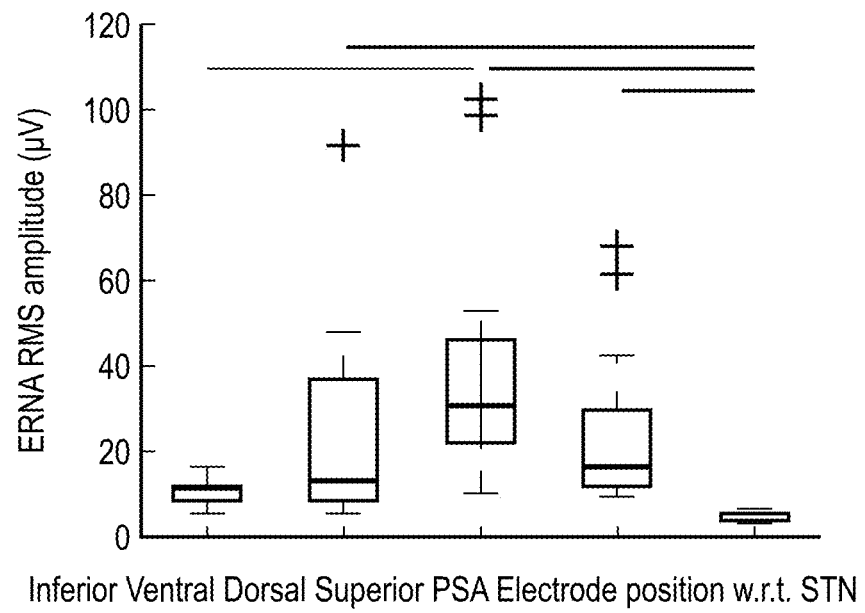
FIG. 24 graphically illustrates the variation in ERNA amplitude relative to electrode position.

ERNA amplitude varied significantly with electrode position (Kruskal-Wallis, H(4)=45.73, p<0.001), with only the inferior electrodes not significantly different from the PSA region (p=0.370) (FIG. 24). Although dorsal electrodes tended to be higher than ventral and superior, they were not significantly different in amplitude from each other. To account for disparity in amplitude across patients due to variation in electrode positioning in the medial-lateral and posterior-anterior planes and underlying differences in patient physiology, we re-analyzed recordings from the STN-DBS electrodes after normalizing responses to the total ERNA amplitude across each hemisphere. After normalization, post hoc comparisons revealed a significant difference in amplitude between dorsal and ventral STN (Kruskal-Wallis, H(3)=14.94, p=0.002; Dunn's method post hoc, dorsal vs ventral: p=0.043, dorsal vs superior: p=0.081, dorsal vs inferior: p=0.002).

These results show that ERNA is localizable to, and varies across, the STN, establishing its utility as a feedback signal for guiding electrode implantation to the most beneficial sites for stimulation. Furthermore, whilst variation in amplitude was the most apparent feature, other ERNA properties, such as frequency, latency, and rate of change, also have potential utility in discriminating STN regions.

ERNA is Modulated by DBS

To investigate whether ERNA was modulated by therapeutically effective DBS, we applied skipped-pulse stimuli of progressively increasing current amplitude (range 0.67-3.38 mA) in blocks of 60-90 s to 10 STN-PD patients (n=19 hemispheres). In general, it was found that the second and subsequent peaks in ERNA were consistently observed to asymptotically increase in latency and spread further apart over time and as stimulation amplitudes increased, consistent with a decrease in the frequency of the resonant activity (FIGS. 5A-5F, 6A-6F, 21A to 21E). In many cases, the latency of the first peak also increased, although this change was not consistent across all recordings. The amplitude of the peaks was also generally observed to vary, often being greater at the beginning of each stimulation block and then gradually diminishing.

To quantify these effects, we calculated the inverse of the difference in latency between the first and second peaks as a representative measure of ERNA frequency. We also calculated the amplitude difference between the first peak and the first trough as a representative measure of ERNA amplitude. We then used averages of the 45-60 s period of each condition as estimates of asymptotic ERNA values for analysis.

Figure 25A:
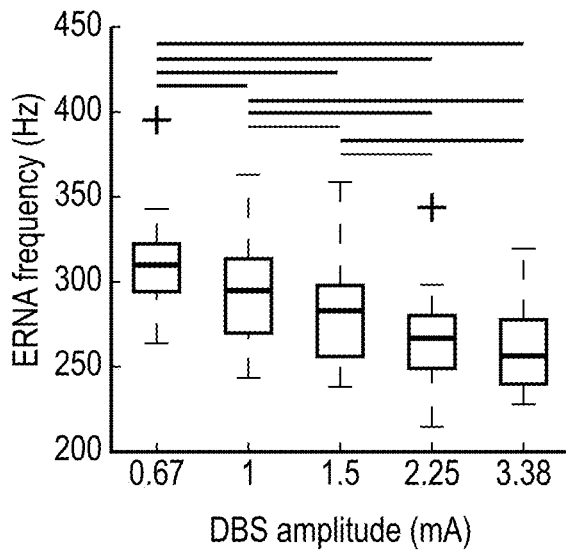
FIG. 25A graphically illustrates ERNA frequency vs DBS amplitude for 19 brain hemispheres.

ERNA frequency significantly decreased across conditions (1-way Repeated Measures (RM) ANOVA, $F(4,94)=45.79$, $p<0.001$). Post hoc comparisons (Holm-Sidak) showed that ERNA frequency significantly decreased with each increasing step of DBS amplitude (FIG. 25A), except from 2.25 mA to 3.38 mA ($p=0.074$). The median frequency was 256 Hz at 3.38 mA, approximately two times the stimulation rate of 130 Hz. It has been proposed that STN-DBS could act by creating a pacing effect within the globus pallidus interna at two times the stimulation rate, due to the immediate excitation of STN axons and inhibition/recovery time course of STN soma.

Figure 25B:
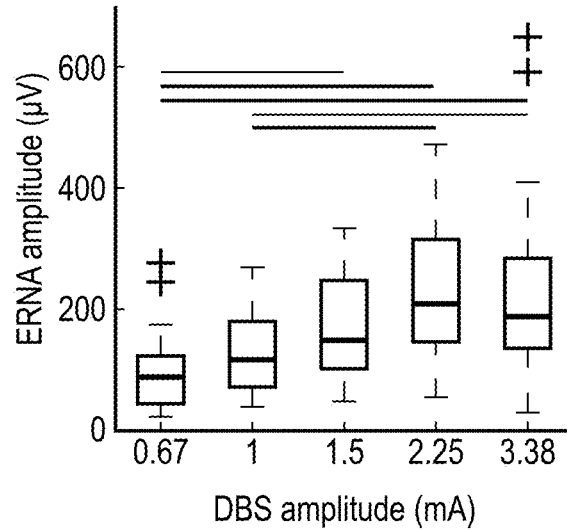
FIG. 25B graphically illustrates ERNA amplitude vs DBS amplitude for 19 brain hemispheres.

ERNA amplitude was also significantly different across conditions (Friedman, $x^2(4)=41.31$, $p<0.001$). Tukey test post hoc comparisons indicated that ERNA amplitude initially increased with DBS amplitude and then plateaued at levels above 1.5 mA (FIG. 25B). While these effects may be related to the therapeutic effects of DBS, they may alternatively or additionally be due to saturation of neural firing in the STN. Due to this, we subsequently focused on ERNA frequency for correlation with therapeutic effects.

ERNA Correlates with Therapeutic Effects

The clinical efficacy of stimulation was confirmed by rating limb bradykinesia and rigidity according to the Unified Parkinson's Disease Rating Scale (UPDRS; items 22 and 23) immediately prior to stimulation and after 60 s at 2.25 mA. Both clinical signs improved significantly at 2.25 mA indicating that DBS was therapeutic (Wilcoxon Signed Rank, bradykinesia: $Z=-3.62$, $p<0.001$, rigidity: $Z=-3.70$, $p<0.001$).

However, time constraints precluded clinical examinations with each step in stimulation intensity. Therefore, to correlate ERNA modulation with patient state, we used beta-band (13-30 Hz) spontaneous LFP activity. Excessive synchronization of oscillations within the beta band has been strongly implicated in the pathophysiology of PD and its suppression has been correlated with improvement in movement impairments of bradykinesia and rigidity.

Figure 25C:
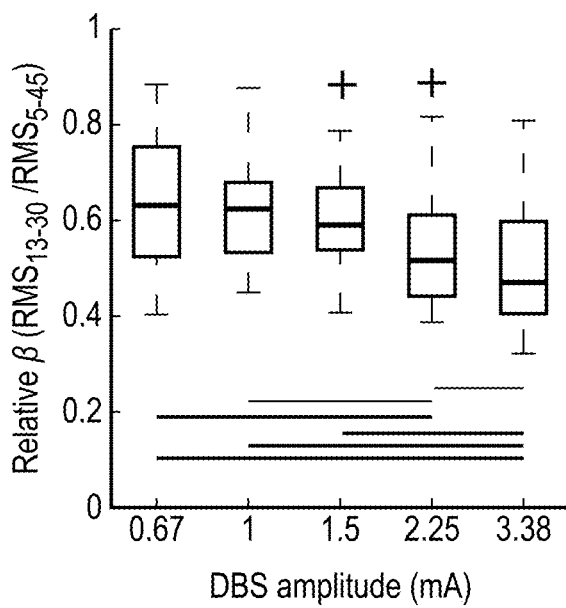
FIG. 25C graphically illustrates Relative beta ($RMS_{13-30\ Hz}/RMS_{4-45\ Hz}$) VS DBS amplitude for 19 brain hemispheres.
Figure 25D:
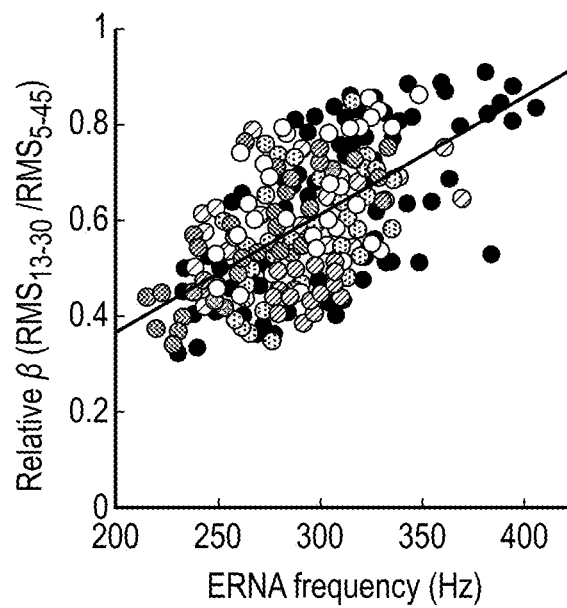
FIG. 25D graphically illustrates Relative beta correlated with ERNA frequency ($\rho=0.601$, $p<0.001$) for 19 brain hemispheres.

Using short-time Fourier transforms we calculated 'relative beta', the RMS amplitude within the 13-30 Hz band divided by that within 5-45 Hz, as a representative measure of beta activity. We then averaged across the 45-60 s period of each stimulation amplitude condition and found relative beta to significantly vary (1-way RM ANOVA, $F(4,89)=18.11$, $p<0.001$). Post hoc tests (Holm-Sidak) showed significant suppression at 3.38 mA compared to all other conditions and at 2.25 mA compared to 0.67 and 1 mA (FIG. 25C). These results are consistent with previous studies showing that beta activity suppression by DBS correlates with improvement in clinical signs, and confirm that stimulation was therapeutically effective at and above 2.25 mA.

To further correlate ERNA frequency with beta activity, and thus therapeutic efficacy, we compared average values for 15 s non-overlapping blocks across each condition (FIG. 25B). ERNA frequency was significantly correlated with relative beta (Pearson product moment, $\rho=0.601$, $n=90$, $p<0.001$).

These results indicate that ERNA is a clinically relevant biomarker. Furthermore, its large amplitude, ranging from 20 µVp-p to 681 µVp-p (median 146 µVp-p), is orders of magnitude larger than spontaneous beta LFP activity, whose absolute values ranged from 0.9 to 12.5 µVRMS (median 2.2 µVRMS). The robustness of ERNA and its distinct and gradually modulated morphology (FIGS. 5, 6, 7, 21) contrast with the inherent variability in beta-band activity across patients and noisy bursting on-off nature of the beta-band signal. ERNA is therefore a more tractable signal to use with a fully-implantable DBS device compared to noisy, low-amplitude LFP measures.

ERNA Modulation Washes Out Following DBS

Immediately before and after the therapeutic skipped-pulse stimulation we also applied 60 s of burst stimulation (hereafter referred to as pre- and post-DBS conditions), in order to monitor changes in activity as therapeutic effects washed out.

Figure 26A:
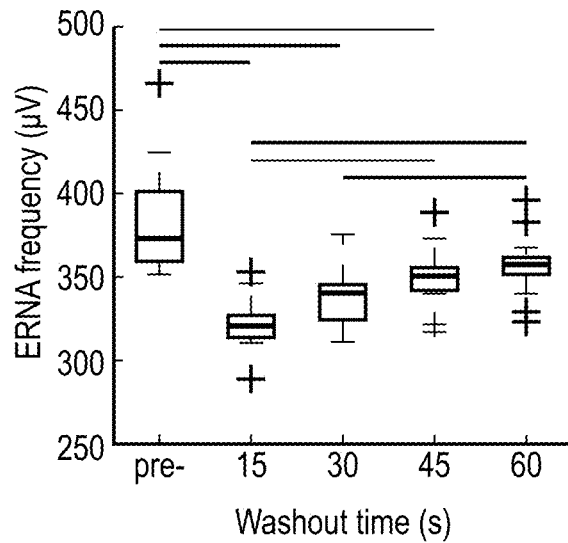
FIG. 26A graphically illustrates ERNA frequency washout over consecutive 15 s periods post-DBS and in the last 15 s pre-DBS for 19 brain hemispheres.
Figure 26B:
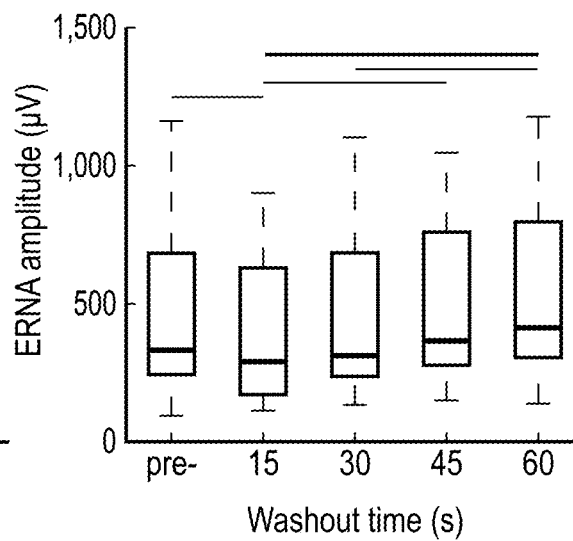
FIG. 26B graphically illustrates ERNA amplitude washout for 19 brain hemispheres.

Generally, ERNA remained relatively stable pre-DBS, indicating the modulatory effects of burst stimulation were minimal. However, immediately post-DBS, ERNA peaks occurred at longer latencies before gradually returning towards their pre-DBS state. To quantify these effects, we averaged post-DBS ERNA frequency and amplitude over 15 s non-overlapping blocks and compared them to the last 15 s pre-DBS. Over all hemispheres tested (n=19), differences were found in ERNA frequency (Friedman, $\chi^2(4)=70.23$, $p<0.001$), with frequencies at all time points significantly reduced compared to the pre-DBS frequency except for the final 45-60 s block (Tukey, $p=0.73$) (FIG. 26A). ERNA amplitude also significantly varied across the time points (Friedman, $\chi^2(4)=31.37$, $p<0.001$), with differences between amplitudes at post-DBS time points indicating a washout of amplitude suppression caused by therapeutic stimulation (FIG. 26B). As the burst stimulus applied was constant across the pre- and post-DBS conditions, the variation observed in ERNA frequency and amplitude can be directly attributed to changes in the state of STN neural circuits as DBS effects washed out. Therapeutically effective DBS therefore modulates both ERNA frequency and amplitude, indicating ERNA has multiple properties that can feasibly be used as biomarkers and as tools for probing mechanisms of action.

Figure 26C:
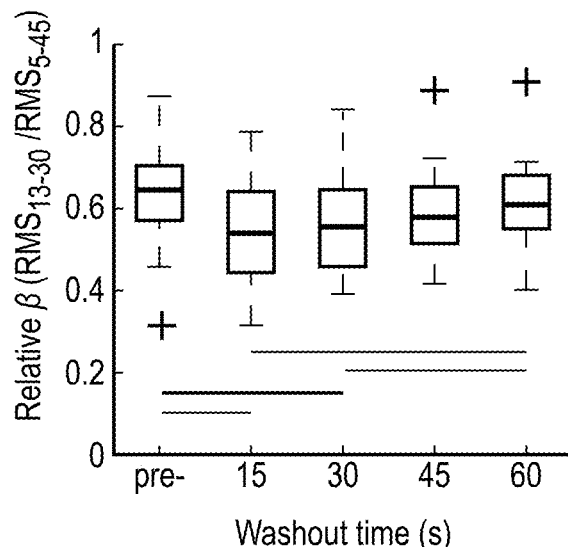
FIG. 26C graphically illustrates Relative beta washout for 19 brain hemispheres.

We then assessed relative beta activity pre- and post-DBS and found it to be significantly different across time points (Friedman, $\chi^2(4)=24.55$, $p<0.001$). Consistent with previous reports, relative beta was significantly decreased immediately post-DBS and washed out to pre-DBS levels after 30 s (FIG. 26C). Supporting the skipped-pulse results, ERNA frequency was significantly correlated with relative beta pre- and post-DBS (Pearson product moment, ρ=0.407, n=152, p<0.001). ERNA amplitude was also correlated with relative beta (Pearson product moment, ρ=0.373, n=152, p<0.001), suggesting it too may have clinical and mechanistic relevance.

We also analyzed spontaneous LFP activity in the high frequency oscillation (HFO) band (200-400 Hz), which overlaps with the observed ERNA frequencies. Changes in the HFO band have been correlated with motor state and effective pharmacological therapy, particularly in conjunction with beta activity, and have been implicated in the mechanisms of action of DBS. Concurrent ERNA and HFO analysis was enabled by the use of burst stimulation, as data could be segmented to only include activity between bursts, thereby providing LFP epochs that were free of stimulation artefacts that can otherwise corrupt the HFO band.

Figure 26D:
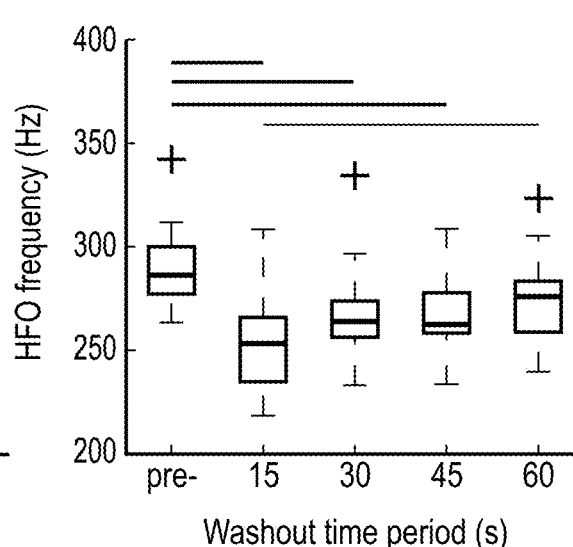
FIG. 26D graphically illustrates Washout in the 200-400 Hz HFO band for 19 brain hemispheres.

As the HFO activity was generally characterized by a broadband peak in frequency, we calculated multitaper spectral estimates and then determined the frequency and amplitude of the peak occurring between 200-400 Hz. Comparing averages across 15 s non-overlapping blocks (FIG. 26D), we found HFO peak frequency to be significantly decreased post-DBS (Friedman, $\chi^2(4)$=45.18, p<0.001), until the final 45-60 s block (Tukey, p=0.077). This washout trend matches that for ERNA frequency, albeit at a lower frequency, with a significant correlation between the two (Pearson product moment, ρ=0.546, n=152, p<0.001). The median HFO peak frequency immediately post-DBS was 253 Hz, comparable to the median ERNA frequency of the therapeutic 3.38 mA condition (256 Hz), suggesting HFO activity occurs at the same frequency as ERNA during the more continuous skipped-pulse stimulation.

No significant differences were found in HFO peak amplitude (Friedman, $\chi^2(4)$=2.11, p=0.72), although it did significantly correlate with ERNA amplitude (Pearson product moment, ρ=0.429, n=152). It is likely that the very small amplitude (<1 μV) of HFO peaks resulted in any modulatory effects being obscured by noise in the recordings.

It will be appreciated by persons skilled in the art that numerous variations and/or modifications may be made to the above-described embodiments, without departing from the broad general scope of the present disclosure. The present embodiments are, therefore, to be considered in all respects as illustrative and not restrictive.

We claim:

1. A method of monitoring neural activity responsive to a stimulus in a brain of a patient, the method comprising:
   a. applying the stimulus to one or more of at least one electrode implanted in or near a target neural structure of the brain;
   b. detecting a resonant response from the target neural structure evoked by the stimulus at one or more of the at least one electrode in or near the target neural structure of the brain, the resonant response having a frequency of between 200 Hz and 500 Hz; and
   c. determining one or more waveform characteristics of the detected resonant response.

2. The method of claim 1, wherein the one or more waveform characteristics are determined based on at least part of a second or subsequent cycle in the detected resonant response.

3. The method of claim 1, wherein the one or more waveform characteristics comprises one or more of the following:
   a) a frequency of the resonant response;
   b) a temporal envelope of the resonant response;
   c) an amplitude of the resonant response;
   d) a fine structure of the resonant response;
   e) a rate of decay of the resonant response;
   f) a delay between the onset of the stimulus and the onset of a temporal feature of the resonant response;
   g) a rate of change of the resonant response.

4. The method of claim 1, further comprising:
   adapting the stimulus based on the one or more determined waveform characteristics of the resonant response.

5. The method of claim 4, wherein the stimulus is adapted based on the time elapsed between adjacent peaks in the resonant response, wherein the stimulus is adapted if the time elapsed between two adjacent peaks in the resonant response is less than a first predetermined time period associated with alleviation of movement symptoms in the patient, wherein the predetermined time period associated with alleviation of movement symptoms in the patient is less than about 3.5 ms.

6. The method of claim 4, wherein the stimulus is adapted based on the time between the stimulus and one or more peaks of the resonant response, wherein the stimulus is adapted if the time elapsed between the stimulus and a peak in the resonant response is between first and second predetermined time periods associated with alleviation of movement symptoms in the patient.

7. The method of claim 4, further comprising:
   correlating the detected resonant response with a template resonant response; and
   adapting the stimulus based on the correlation.

8. The method of claim 1, wherein the stimulus comprises a patterned signal comprising a plurality of bursts separated by a first time period, each burst comprising a plurality of pulses separated by a second time period, wherein the first time period is greater than the second time period and wherein the detecting is performed during one or more of the first time periods.

9. The method of claim 1, further comprising:
   applying a second stimulus to a target neural structure in the brain;
   detecting a second resonant response from the target neural structure evoked by the second stimulus at one or more of the at least one electrode implanted in or near the target neural structure;
   determining one or more second waveform characteristics of the detected second resonant response.

10. The method of claim 1, further comprising:
    determining whether one or more of the at least one electrode is positioned in the target neural network based on the detected resonant response.

11. The method of claim 10, wherein the at least one electrode comprises a plurality of electrodes, and wherein the steps of applying the stimulus, detecting a resonant response and determining one or more waveform characteristics of the detected resonant response are repeated using different combinations of the at least one electrode to generate a profile of resonant responses.

12. The method of claim 1, further comprising:
    repeating the steps of applying the stimulus, detecting a resonant response and determining one or more waveform characteristics of the detected resonant response.

13. The method of claim 1, further comprising:
    selecting one or more of the at least one electrode to use for therapeutic stimulation of the target neural structure based on the one or more waveform characteristics; and applying a therapeutic stimulus to the target neural structure via the selected one or more of the at least one electrode.

14. The method of claim 1, wherein the one or more of the at least one electrode used to apply the stimulus comprises at least two electrodes and/or wherein the one or more of the at least one electrode used to detect the resonant response comprises at least two electrodes.

15. The method of claim 1, wherein the neural target structure is part of the cortico-basal ganglia-thalamocortical circuit.

16. The method of claim 1, wherein the neural target structure is the subthalamic nucleus, globus pallidus interna, substantia nigra pars reticulata, pedunculopontine nucleus.

17. The system of claim 16, wherein the one or more waveform characteristics are determined based on at least part of a second or subsequent cycle in the detected resonant response.

18. The system of claim 17, wherein the stimulus is adapted based on the time elapsed between adjacent peaks in the resonant response, wherein the stimulus is adapted if the time elapsed between two adjacent peaks in the resonant response is less than a first predetermined time period associated with alleviation of movement symptoms in the patient, wherein the predetermined time period associated with alleviation of movement symptoms in the patient is less than about 3.5 ms.

19. The system of claim 17, wherein the stimulus is adapted based on the time between the stimulus and one or more peaks of the resonant response, wherein the stimulus is adapted if the time elapsed between the stimulus and a peak in the resonant response is between first and second predetermined time periods associated with alleviation of movement symptoms in the patient.

20. The system of claim 17, wherein the stimulus comprises a patterned signal comprising a plurality of bursts separated by a first time period, each burst comprising a plurality of pulses separated by a second time period, wherein the first time period is greater than the second time period and wherein the detecting is performed during one or more of the first time periods.

21. The system of claim 16, wherein the one or more waveform characteristics comprises one or more of the following:
  a) a frequency of the resonant response;
  b) a temporal envelope of the resonant response;
  c) an amplitude of the resonant response;
  d) a fine structure of the resonant response;
  e) a rate of decay of the resonant response;
  f) a delay between the onset of the stimulus and the onset of a temporal feature of the resonant response;
  g) a rate of change of the resonant response.

22. The system of claim 16, wherein the processing unit is configured to:
  control the signal generator to adapt the stimulus based on the one or more determined waveform characteristics of the resonant response.

23. The system of claim 16, wherein the processing unit is configured to:
  estimate a degree of progression of a disease associated with the patient or an effect of a therapy provided to the patient based on the one or more waveform characteristics and one or more second waveform characteristics, the one or more second waveform characteristics determined based on a second resonant response detected after the resonant response.

24. The method of claim 1, wherein the patient is under general anaesthetic.

25. The method of claim 1, wherein detecting a resonart response from the target neural structure evoked by the stimulus comprises detecting the resonant response at two or more of the at least one electrode; wherein the method further comprises comparing the one or more waveform characteristics of the detected resonant response detected at the two or more of the at least one electrode.

26. The method of claim 25, further comprising adapting the stimulus based on the comparison.

27. A neurostimulation system, comprising:
  a lead having at least one electrode adapted for implantation in or near a target neural structure in a brain of a patient;
  a signal generator selectively coupled to one or more of the at least one electrode and configured to generate a stimulus to stimulate the target neural structure;
  a measurement device selectively coupled to one or more of the at least one electrode and configured to detect a resonant response from the target neural structure evoked by the stimulus, the resonant response having a frequency of between 200 Hz and 500 Hz;
  a processing unit coupled to the measurement device and configured to determine one or more waveform characteristics of the detected resonant response.

28. The system of claim 27, wherein detecting a resonant response from the target neural structure evoked by the stimulus comprises detecting the resonant response at two or more of the at least one electrode; wherein the method further comprises:
  comparing the one or more waveform characteristics of the detected resonant response detected at the two or more of the at least one electrode; and
  adapting the stimulus based on the comparison.

* * * * *